(12) United States Patent
Patel

(10) Patent No.: US 11,365,382 B2
(45) Date of Patent: Jun. 21, 2022

(54) BIOREACTOR SYSTEM AND METHOD THEREOF

(71) Applicant: OMNIBRX BIOTECHNOLOGIES PRIVATE LIMITED, Gujarat (IN)

(72) Inventor: Ravindrakumar Dhirubhai Patel, Ahmedabad (IN)

(73) Assignee: OMNIBRX BIOTECHNOLOGIES PRIVATE LIMITED, Ahmedabad (IN)

( * ) Notice: Subject to any disclaimer, the term of this patent is extended or adjusted under 35 U.S.C. 154(b) by 675 days.

(21) Appl. No.: 15/578,635

(22) PCT Filed: Oct. 4, 2016

(86) PCT No.: PCT/IN2016/050336
§ 371 (c)(1),
(2) Date: Nov. 30, 2017

(87) PCT Pub. No.: WO2017/158611
PCT Pub. Date: Sep. 21, 2017

(65) Prior Publication Data
US 2018/0187139 A1      Jul. 5, 2018

(30) Foreign Application Priority Data

Mar. 14, 2016   (IN) .............................. 201621008865

(51) Int. Cl.
*C12M 3/06* (2006.01)
*C12M 1/12* (2006.01)
(Continued)

(52) U.S. Cl.
CPC ............ *C12M 27/14* (2013.01); *C12M 23/40* (2013.01); *C12M 25/06* (2013.01); *C12M 27/20* (2013.01);
(Continued)

(58) Field of Classification Search
CPC ...... C12M 23/40; C12M 25/06; C12M 27/14; C12M 27/20; C12M 41/14; C12M 41/26; C12M 41/32; C12M 41/40; C12M 41/42
See application file for complete search history.

(56) References Cited

U.S. PATENT DOCUMENTS

| 3,407,120 A | 10/1968 | Weiss et al. |
| 3,933,585 A | 1/1976 | McAleer et al. |

(Continued)

FOREIGN PATENT DOCUMENTS

| GB | 1097669 A | 1/1968 |
| GB | 1393654 A | 5/1975 |

(Continued)

OTHER PUBLICATIONS

The International Search Report and Written Opinion issued in PCT/IN2016/050336 dated Mar. 24, 2017.
(Continued)

*Primary Examiner* — Michael L Hobbs
(74) *Attorney, Agent, or Firm* — Acuity Law Group, PC; Michael A. Whittaker

(57) ABSTRACT

The present invention relates to bioreactor system and method thereof wherein support matrix (2) comprises at last one central shaft and plurality of peripheral shaft being radially surrounds central shaft. Arrays of discs (11) are mounted along the shaft by defining interspatial vicinities between two successive plates. Thus, discs mounted on peripheral shafts are rotated within the interspatial vicinity of discs of central shaft to ensures sufficient mixing and avoid stagnant fluidic zones which is created when discs are mounted closely apart from each other on shafts. Further, plurality of deflector vanes that are axially provided along the length of the central shaft to redirect substantially co-axial direction fluid flow into interior of culture vessel and more specifically towards the central axis. Thus, biore-
(Continued)

actor system provides scalable and disposable bioreactor with efficient mixing and homogeneous conditions and thereby supports high density growth and maintenance of cells and other biological material.

42 Claims, 17 Drawing Sheets

(51) Int. Cl.
    *C12M 1/00* (2006.01)
    *C12M 1/34* (2006.01)
(52) U.S. Cl.
    CPC ............ *C12M 41/14* (2013.01); *C12M 41/26* (2013.01); *C12M 41/32* (2013.01); *C12M 41/40* (2013.01); *C12M 41/42* (2013.01)

(56) References Cited

U.S. PATENT DOCUMENTS

| | | | |
|---|---|---|---|
| 4,065,359 A | 12/1977 | Hurni | |
| 4,343,904 A | 8/1982 | Birch et al. | |
| 5,587,298 A * | 12/1996 | Horigane | C12M 27/00 366/300 |
| 8,809,037 B2 * | 8/2014 | Haley, III | C02F 3/302 435/262.5 |
| 2010/0075405 A1 * | 3/2010 | Broadley | C12M 41/22 435/286.1 |
| 2011/0195462 A1 * | 8/2011 | Banks | C12M 25/14 435/101 |
| 2011/0281343 A1 * | 11/2011 | Gay | C12M 27/12 435/287.1 |
| 2012/0040449 A1 * | 2/2012 | Zambaux | C12M 27/02 435/302.1 |
| 2012/0196336 A1 * | 8/2012 | McCutchen | A01K 61/59 435/134 |
| 2013/0337548 A1 * | 12/2013 | Sims | C12M 27/10 435/257.1 |
| 2014/0134672 A1 * | 5/2014 | Tuttman | C12M 41/40 435/47 |
| 2014/0227769 A1 * | 8/2014 | Strobbe | C12N 5/0607 435/287.1 |

FOREIGN PATENT DOCUMENTS

| | | | |
|---|---|---|---|
| GB | 2058131 A * | 4/1981 | ............ C12M 25/06 |
| GB | 2058131 A | 4/1981 | |
| JP | H04126068 U | 11/1992 | |
| JP | H04335882 A | 11/1992 | |
| JP | H7-8260 A | 1/1995 | |
| JP | H7-75550 A | 3/1995 | |
| JP | 2014519825 A | 8/2014 | |
| SG | 11201807903 T | 10/2018 | |
| WO | 2011097566 A1 | 8/2011 | |
| WO | 2016013069 A1 | 1/2016 | |
| WO | 2016026932 A1 | 2/2016 | |

OTHER PUBLICATIONS

Office Action issued in Israeli Patent Application No. 261716 dated Jan. 13, 2020—incl Eng lang summary (12 pages total).
Response to Office Action issued in Israeli Patent Application No. 261716 dated May 12, 2020—Engl lang transl only (11 pages).
Office Action Issued in Canadian Patent Application No. 3,017,434 dated Jul. 24, 2019 (5 pages).
Response to Office Action issued in Canadian Patent Application No. 3,017,434 dated Jan. 24, 2020 (41 pages).
Search Report Issued in Singapore Patent Application No. 11201807903T dated Oct. 18, 2019 (3 pages).
Response to Search Report Issued in Singapore Patent Application No. 11201807903T dated Nov. 11, 2019 (8 pages).
Office Action issued in Brazilian Patent Application No. BR112018068711-1 dated Dec. 16, 2019—incl Eng lang only (4 pages).
Office Action issued in Japanese Patent Application No. 2019-500050 dated Dec. 4, 2019—incl Eng lang transl (9 pages total).
Response to Office Action issued in Japanese Patent Application No. 2019-500050 dated Mar. 9, 2020—incl Eng lang transl (23 pages total).
Office Action Issued in Great Britain Patent Application No. 1816573.8 dated May 15, 2020 (3 pages).

\* cited by examiner

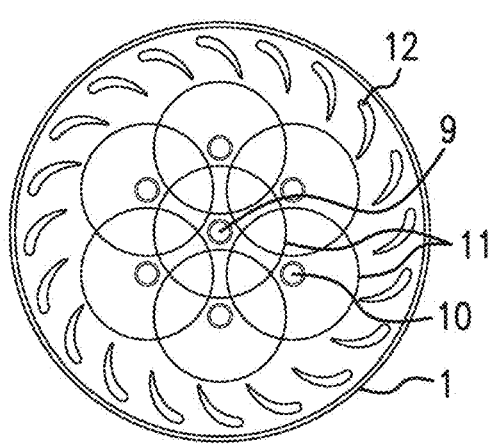
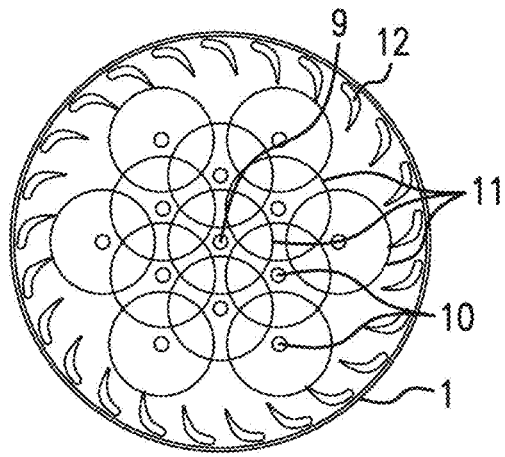
Fig.8 (e)        FIG.8(f)
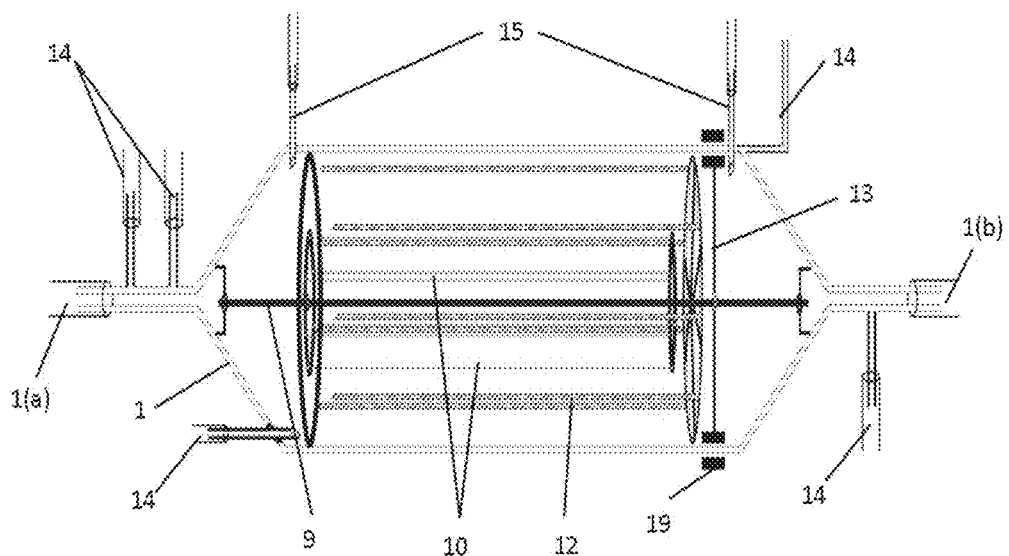
Fig.9

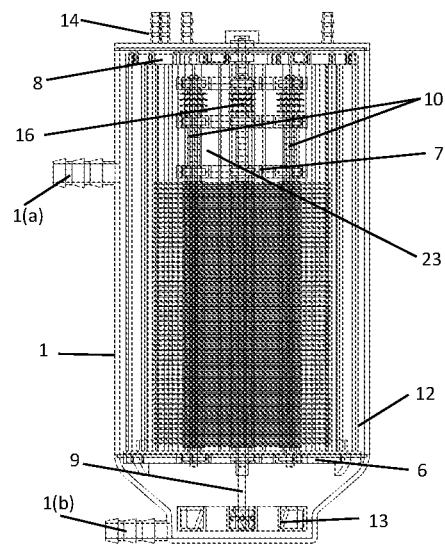
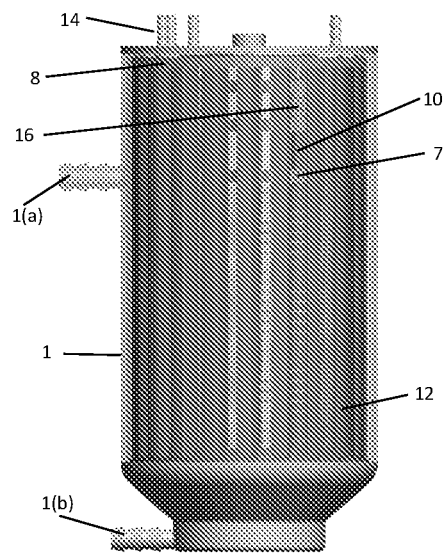
Fig. 15(a)   Fig. 15(b)
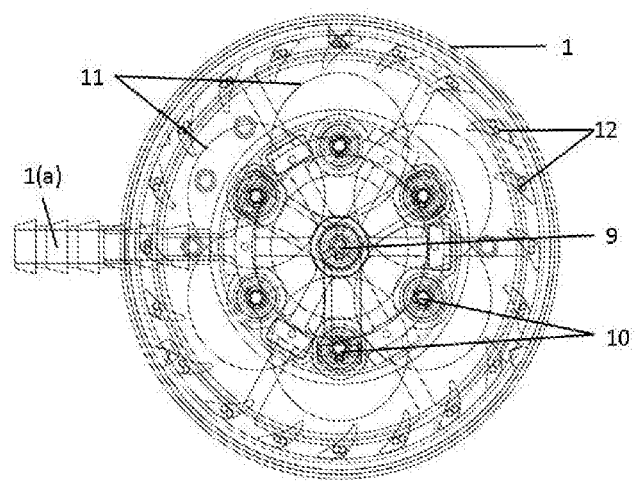
Fig. 15(c)

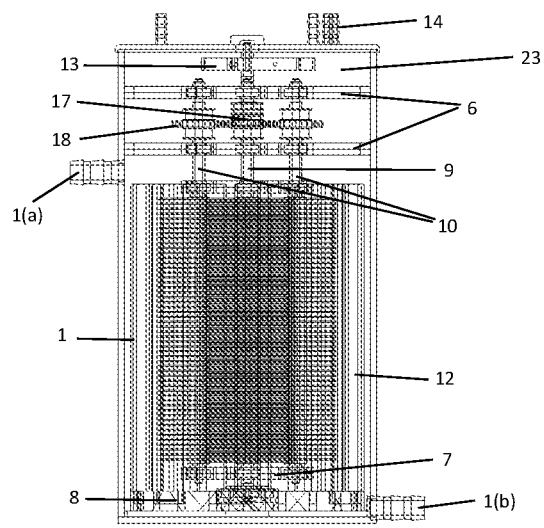
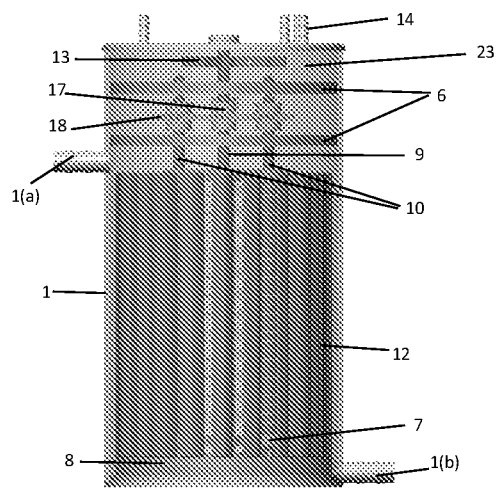
Fig. 16(a)  Fig. 16(b)
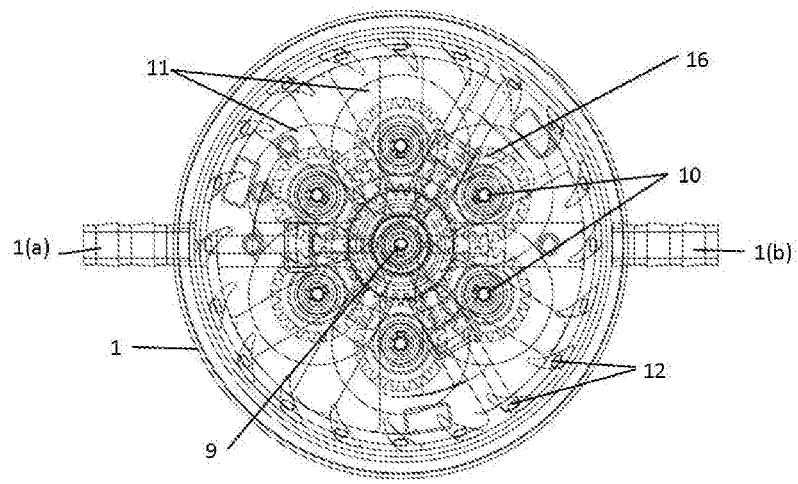
Fig. 16(c)

BIOREACTOR SYSTEM AND METHOD THEREOF

FIELD OF THE INVENTION

The present invention relates to a bioreactor and more particularly it relates to a system and method for cultivation and supporting large scale culturing of various types of cells and processing of materials on scalable support matrix.

BACKGROUND OF INVENTION

Bioreactor systems are increasingly being used for synthesis of the biological material. Among that, mammalian cell lines are commonly employed by the biopharmaceutical industry to produce various recombinant proteins for diagnostic and therapeutic applications. Large-scale, high-density cell cultures are needed to meet the growing market demands. To improve product economics, optimization of cell culture conditions to maximize viable cell densities and to prolong culture lifetime to increase final product titers, have become the most important goals in large-scale process development. The pressure in biotechnology production today is for greater speed, lower costs and more flexibility. Ideally, a production unit should be compact (requires less investment) and modular.

The demand for therapeutic proteins derived from mammalian cell culture continues to grow, as newer products are being approved. Some of the newer products such as antibodies and receptor binding proteins need to be administered in higher doses and this necessitates production of larger quantities than was the case with earlier products. Consequently, there is a continuing need to increase the productivity of mammalian cell culture bioreactors with minimal investment in additional equipment.

Mammalian cells are the preferred expression system for making recombinant proteins for human use because of their ability to express a wide variety of proteins with a glycosylation profile that resembles that of the natural human protein.

Production in stirred bioreactors is relatively simple to scale-up, but requires large culture volumes (i.e. 10-20 $m^3$) to compensate for the relatively low cell densities that are attained. Typically, the cell density in suspension culture is between $10^6$ and $10^7$ cells·$ml^{-1}$. Compared to batch culture in stirred tanks, nearly 10-fold higher cell densities (i.e. $10^7$-$10^8$ cells·$ml^{-1}$) can be attained in perfusion cultures in which the medium is perfused at an appropriate rate in a constant volume culture and the cells are retained in the bioreactor by various means.

Adapting stirred tank bioreactor technology for cell culture is a futile exercise because the design exhibits intrinsically high local shear rates to suspended cells, making scale up very difficult and also time period required for the suspension adaptation and selection of desired clone is countable for process establishment and economics. With fed-batch bioreactors, cells are cultured using media-filled bioreactors and harvested in batches after (for example) 8 to 21 days. By contrast, perfusion bioreactors involve continuous culture, feeding, and withdrawal (harvesting) of spent media generally for much longer periods, even months. Cells are held within the latter either by being bound to grow on capillary fibers or other membranes or retained in the bioreactor though use of special filtration or separation systems.

Given the relative fragility of many cells in culture, reactor design becomes an important issue in enhancing process economics. Among the requirements of animal cells towards the cultivation environment, hydrodynamic shear stress is an important aspect to consider and to decrease as much as possible. On the other hand, sufficient mixing, e.g., by a stirrer, has to be provided to maintain homogeneous conditions inside the bioreactor and to rapidly distribute feeds such as base, medium in continuous processes or antifoam agent.

The majority of the cells derived from vertebrates, with the exception of hematopoietic cell lines and a few others are anchorage-dependent and have to be cultured on a suitable substrate that is specifically treated to allow cell adhesion and spreading (i.e., tissue-culture treated). However, many cell lines can also be adapted for suspension culture. Similarly, most of the commercially available insect cell lines grow well in monolayer or suspension culture. Efficiency of the Anchorage dependant cell culture system is based on increasing the available surface area by using plates, spirals, ceramics and microcarriers. Roux flask, roller bottle, multi-tray unit, synthetic hollow fiber cartridge, opticell culture system, plastic film, bead bed reactors, microcarrier cultures, etc., are the various culture vessels currently in used. All above culture vessels provide increased surface area due to the vessel design and use of multiple units.

To produce large quantities of non-anchorage dependent cells, the cells are usually grown in suspension in a nutrient liquid medium that is stirred to ensure that each cell is adequately bathed in nutrients, and that metabolic wastes are carried away from the cell. A certain fraction of the cells is destroyed by impact with the impeller or by high shear. Harvesting cells from conventional suspension culture requires special supplemental equipment such as centrifuges or micro-porous filters. Also cell concentration per cubic centimeter of nutrient liquid is relatively low.

Recent market survey reports on Biopharmaceutical Manufacturing Capacity & Production, showing that biopharmaceutical companies have uniformly increased their budgets in essentially all areas related to bioprocessing. Survey data also indicate that industry professionals are becoming impatient with an apparent lack of innovation in bioprocessing equipment, notably in bioreactor offerings, and that much of the industry remains unaware of recent advances in perfusion bioreactors.

Because of a high cell density, the productivity of perfusion systems can be as much as 10-fold greater than the productivity of a comparable fed-batch bioreactor. In other words, a 2 $m^3$ perfusion culture would be roughly equivalent to a 20 $m^3$ fed-batch culture. Disadvantages of perfusion culture include their complexity and possible difficulty in scale-up. For example, large-scale cell retention devices for suspension cells are not yet entirely satisfactory.

Various kinds of cell culturing systems have been developed for enhancing the growth of cells. The list of such patents and limitation associated therewith is given below. British Patent No. 1,097,669 describes a tissue culture propagator comprising a vessel for the growth medium and a series of spaced-apart plates arranged as a stack on a rack within the vessel. The stack of plates remains stationary within the vessel and the necessary circulation of the growth medium within the vessel is achieved by means of an air lift pump. In use, the vessel is filled to the required degree with growth medium inoculated with the cells it is desired to grow which are allowed to settle on the surface of the plates and the required circulation within the vessel is produced by an air lift pump or by magnetic or vibratory agitation. A modified apparatus of this type has been proposed by Biotec AB, of Sweden which apparatus comprises a stack of discs mounted on a rotatable axial shaft within a cylindrical vessel. In use, this apparatus is first positioned vertically, i.e. with the axial shaft at right angles to the working surface, the vessel is filled with nutrient medium, cells are plated onto the disc surfaces and then the apparatus is placed in a horizontal position, about half of the nutrient medium is removed from the vessel and the shaft and stack of discs rotated so that only the lower section of the discs are at any one time passing through growth medium lying in the vessel.

In British Pat. No. 1,393,654, a further modification of the Biotec apparatus is proposed in which the ratio of disc diameter to internal vessel diameter is from 0.80:1 to 0.90:1 and in addition it is preferred that the distance between the edge of the discs and the internal wall of the vessel is from ½ to ¾ of an inch (from 1.27 to 1.905 cm). It is also preferred that the ratio of total surface area of the discs to the volume of the vessel is from 5.5:1 to 6.0:1. In view of the nature of the operation of this apparatus, and of the Biotec apparatus, rotation of the shaft needs to be slow to minimize the shear forces produced on the cells as the discs rotate in and out of the growth medium. Rotation speeds of the order of 0.5 rpm have been suggested as a practical maximum for this apparatus. Lower speeds are frequently used.

Weiss and Schleicher in U.S. Pat. No. 3,407,120 invented a method and apparatus for growing living cells, the apparatus comprising' a plurality of spaced-apart plates upon which the cells may attach and proliferate and it is disposed within a vessel or tank-type container containing nutrient medium. Means for mixing and oxygenating of the medium are provided. Cells can be grown within the apparatus by planting the medium with cells desired to be grown and oxygenating and circulating the medium until a substantially confluent monolayer of cells is formed on the surface of the plates.

In U.S. Pat. No. 3,933,585 William J. McAleer's primary objective was to increase the yield and reduce production costs by increasing the surface area or cell plating area to volume of medium ratio in order to obtain the highest yield of cells and vaccine in the smallest volume. Their invention was further advancement of the multiplate machine produced by Biotic A. B. of Sweden. The surface area to volume ratio nearby 3.0 cm2/ml was achieved in the Biotec apparatus. William J. McAleer had unexpectedly discovered that significant increases in the yield of cells and vaccines was obtained by using a device which has a surface area to volume ratio of from about 1.7 cm2/ml to about 2.2 cm2/ml. He had also discovered that yields of cells and vaccines can be obtained which were significantly greater than the yields of cells and vaccines which are produced using any of the aforementioned devices by utilizing multi-plate propagators which have a critical plate diameter to internal tank diameter ratio, or which have a critical distance between the periphery of the plates and the inner wall of the tank. This critical diameter ratio may be from about 0.80 to about 0.90, preferably from about 0.82 to about 0.84 as compared to 0.96 in the Biotec unit. They disclosed, a propagator which comprises a cylindrical stainless steel tank having flanges and at each end thereof.

In the rotary type of apparatus described above, the need to move the apparatus from the vertical to the horizontal is a real disadvantage when large scale apparatus is considered. Circulation of the growth medium using an air lift pump cannot be efficiently performed without unacceptable foaming of the medium which may necessitate the addition of anti-foam agents which may adversely influence the growth and metabolism of tissue culture cells. The necessary slow rotational speeds makes the mixing in of subsequently added growth medium constituents and other reagents inefficient and also continuous measurement of conditions within the vessel cannot be made reliable, because poor mixing dictates that the vessel contents cannot function as a homogeneous system.

In U.S. Pat. No. 4,343,904, Birch et. al disclosed a bioreactor system in which animal cells are grown in a vertically disposed cylindrical vessel containing a stack of parallel spaced-apart discs inclined at least 5° from the horizontal and mounted to a rotatable axial shaft. The vessel is closed by a top plate having a plurality of inlets and a bottom plate with an outlet, and contains an external pumping loop for circulating contents of the vessel from the bottom to the top of the vessel. Growing of the cells is carried out by substantially filling the vessel with a mixture of animal cells and growth medium, allowing the cells to settle on the disc surfaces and then rotating the axial shaft at a speed of at least 5 rpm while continuously circulating the vessel contents from the bottom to the top of the vessel. This process and apparatus provides efficient mixing and ensures a homogeneous system within the vessel.

The invention disclosed in U.S. Pat. No. 5,168,058 relates to packing material for use in the cultivation of anchorage-dependent cells, which require a solid surface for proliferation. The packing material of the invention is provided in the form of units of curved sheet material, which individual units generally have a thickness of about 0.05 mm to 0.25 mm, the other dimensions being of the order of one to a few millimeter maximum dimensions. Various shapes can be used, such as twisted rectangles, segments of cylinders, convulated ribbons, twisted shapes, etc.

Developed by GlenMills Inc., Zellwerk cell culture system with Z®RP bioreactors are easy to assemble and handle. They are usually operated in perfusion mode and host large amounts of cells in very small volumes. The centerpiece is a magnetic coupled rotating axis mounted with the cell- or tissue carrier of choice exposing cells to medium and overlay alternately. From highly porous Sponceram® discs to implant scaffolds and all kinds of supports can be installed in a Z®RP bioreactor giving rise to a vast variety of culturing options. In all configurations best possible aeration and feeding is guaranteed. The gentle rotational motion stimulates cells and tissues to adhere and proliferate fast without being stressed by shear forces. Cell populations stay viable and express large amounts of extra cellular matrix. Three-dimensional high density cultivation can be extended to many months without decrement of viability or expression productivity. Harvest of adherent cells is easily achieved employing specific rotation programs in combination with detaching solutions.

In response to the lack of suitable large-scale expansion and recovery systems for adherent cells, PALL life sciences (originally developed by ATMI Life Science) has developed a new 2-D bioreactor, the Integrity™ Xpansion™ Multiplate Bioreactor which contains a series of stacked discs or plates which are mounted vertically one above another and liquid media flow through the internal space created by discs stacking in a cylindrical vessel. Due to its large surface area and multiplate design, the system enables production of large amounts of cells in a process easily adapted from traditional T-flask or stacked-tray methods. The Xpansion bioreactor was designed to enable adherent cell growth in the same conditions and surfaces than in T-flasks. Cells adhere and grow on the stacked polystyrene plates. % DO and pH are controlled by equilibration of media with a gaseous phase where concentration of $O_2$ and $CO_2$ is controlled. The gases diffuse through the wall of very thin silicon tubing placed in the central column. Media circulation is generated by a centrifuge pump controlling the flow rate to adapt it to appropriated shear stress requirements.

A bioreactor system that can provide extremely high productivity within a compact size is the packed-bed bioreactors (PBRs). Packed-beds have been used widely for perfusion culture of immobilized mammalian cells. This invention focuses on the prospects of PBRs as a potential future preferred production tool for making cell-culture derived products. PALL life sciences (originally developed by ATMI Life Science) have developed iCELLis packed bed bioreactors. Central to the iCELLis bioreactor technology is the use of a compact fixed-bed, filled with custom macro carriers. This matrix is made of medical grade polyester micro fibers and provides large surface area available for cell growth.

Except the advancement in achieving higher cell densities and increased productivity through improved mixing conditions, yet, the efficient mass transfer and industrially suitable scalability of the systems remains partly unsolved/unresolved issue.

It is being critical to recognize & meet the special demands of in-vitro cell culture and thus is essential to design a novel device to satisfy these needs. These demands include shear sensitivity of cultured animal cells, use of bubble free aeration, relatively small oxygen uptake rate, and ease of operation with reduced chances of contaminations or other manual handling errors.

Hence, it is desperately needed to invent a device and method accommodating high density growth of cultured cells within small culture volume with efficient nutrients and oxygen distribution within culture vessel without damaging cells by fluid or impeller blade shear and gas bubbles.

OBJECT OF THE INVENTION

The main object of present invention is to provide a bioreactor system and method thereof that provides scalable, preferably disposable bioreactor capable of providing efficient mixing and homogeneous suspension and thereby supports high density growth and maintenance of cells and biological material.

Another object of present invention is to provide a bioreactor system and method thereof that renders shear sensitivity by conciliation without gas sparging of cultured animal cells inside the culture vessel, bubble free aeration, relatively small oxygen uptake rate and ease of operation with reduced chances of contaminations or other manual handling errors.

Yet another object of present invention is to provide a bioreactor system and method thereof that provide a sterile, ready to use disposable cultivation vessel to reduce labor cost and production time.

Further object of present invention is to provide a bioreactor system and method thereof that is simple in construction and reduce mechanical and instrumentation complexity and is commercially scalable.

One more object of present invention is to provide a bioreactor system and method thereof that allow accommodation of large amount of surface area within the small culture volume while maintaining efficient mixing and nutrient homogeneity within the culture vessel.

One more object of present invention is to provide a bioreactor system and method thereof that provides in-line monitoring and control on process variables like pH, dissolved oxygen, temperature etc. Online sampling for measurement of the nutrients, metabolic by-products, and feed addition may be feasible.

One more object of present invention is to provide a bioreactor system and method thereof wherein the nutrient medium contained within the culture vessel can be exchanged, sampled, or modified with or without interrupting the support matrix movement.

One more object of present invention is to provide a bioreactor system and method thereof that is used for producing one or more chemical compounds.

One more object of present invention is to provide a bioreactor system and method thereof that is used for treating the effluent for waste water and for remediation of industrial fluid waste treatment.

One more object of present invention is to provide a bioreactor system and method thereof that is used for enzymatic treatment of variety of substrates and compounds.

SUMMARY OF THE INVENTION

The present invention relates to a bioreactor system and method for operating the same for handling of biological material and supporting large-scale continuous or batch culturing of biological cells by culturing, entrapping or encapsulating cells or biological material directly on the support matrix. The bioreactor system of the present invention comprises the culture vessel, support matrix, a fluid pumping means, gas exchange module and a main conduit for forming a closed circulation loop of nutrient medium. Said support matrix is disposed within the interior of the culture vessel. The support matrix comprises at last one central shaft and plurality of peripheral shaft being radially surrounds the central shaft. Said central and peripheral shafts are rotationally supported by the support framework and shaft mounting frame. In present invention, a plurality of disc is mounted along the shaft to define interspatial vicinities between two successive plates. Thus, the disc mounted on the peripheral shaft are rotated within the interspatial vicinity formed between the successive discs of central shaft thereby ensures sufficient mixing and avoid the stagnant fluidic zones which can be created when the discs are mounted closely apart from each other on the shafts. Further, plurality of deflector vanes that are axially provided along the length of the central shaft to redirect the substantially co-axial direction fluid flow into the interior of the culture vessel and more specifically towards the central axis. Thus, the bioreactor system according to present invention provides a scalable, preferably disposable bioreactor capable of providing efficient mixing and homogeneous suspension and thereby supports high density growth and maintenance of cells and biological material.

BRIEF DESCRIPTION OF THE DRAWING

Objects and advantages of the invention will be apparent from the following detailed description taken in conjunction with the accompanying figures of the drawing wherein:

FIG. 1a illustrates a perspective view of bioreactor system with horizontally oriented culture vessel according to present invention.

FIG. 1b shows a schematic representation of bioreactor system shown in FIG. 1a.

FIG. 9 illustrates a sectional view of the culture vessel with additional port and conduits according to present invention.

FIGS. 15a, 15b and 15c illustrates a detailed view of vertically oriented culture vessel with magnetic rotation means for shaft rotation located at bottom and baffle rotating means for baffle mounting plate located at top of the vessel thereof according to present invention.

FIGS. 16a, 16b and 16c illustrates a detailed view of vertically oriented culture vessel with magnetic rotation means for shaft rotation located at top and baffle rotating means for baffle mounting plate located at bottom of the vessel thereof according to present invention.

DETAILED DESCRIPTION OF THE INVENTION

Figure 1:
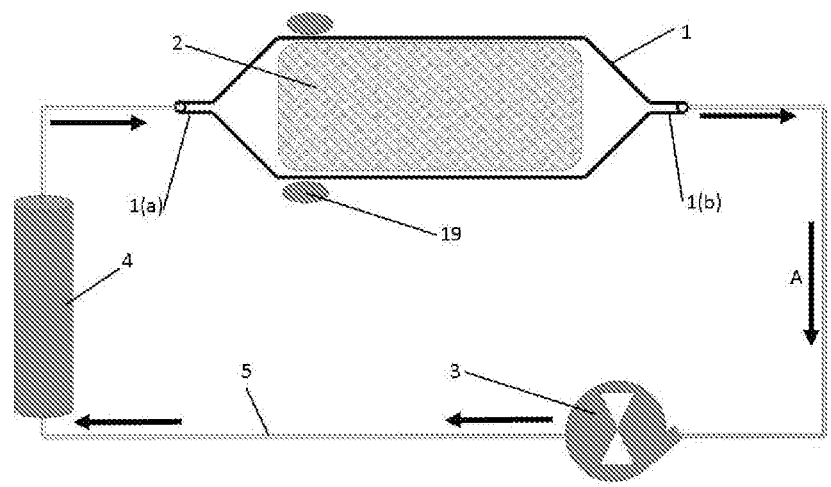
Figure 1:
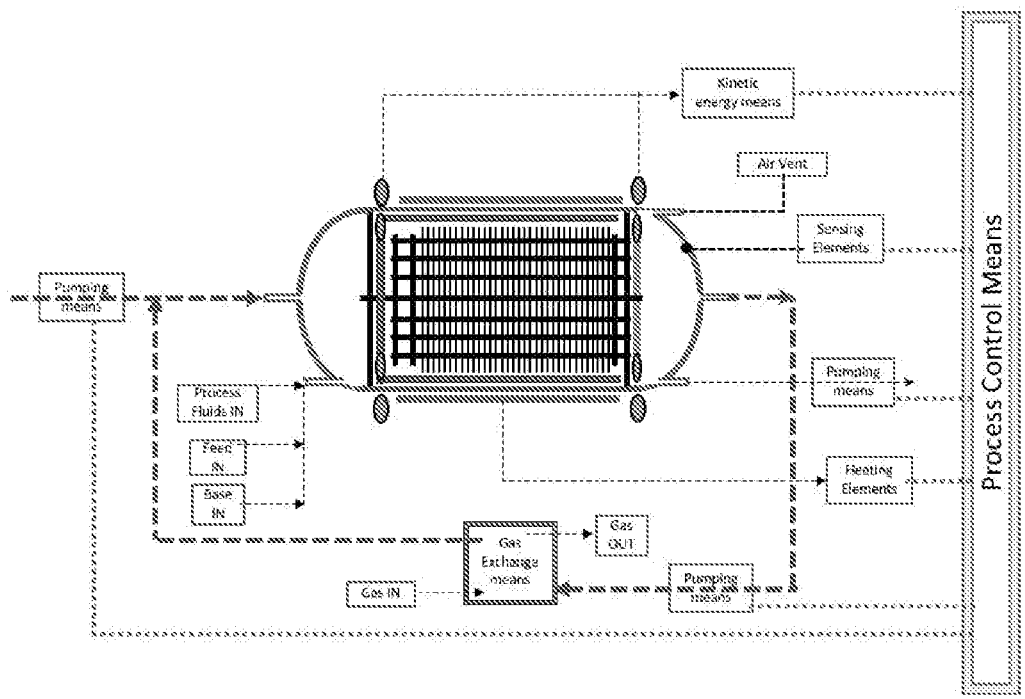

Before explaining the present invention in detail, it is to be understood that the invention is not limited in its application to the details of the construction and arrangement of parts illustrated in the accompany drawings. The invention is capable of other embodiments, as depicted in different figures as described above and of being practiced or carried out in a variety of ways. It is to be understood that the phraseology and terminology employed herein is for the purpose of description and not of limitation.

Further, it is to be also understood that the phrase as used herein, "biological material" mean, but are not limited to, any particle(s), substance(s), extract(s), mixture, and/or assembly derived from or corresponding to one or more organisms, cells, and/or viruses. It will be apparent to one skilled in the art that cells which may be cultured in an automated cell management system comprise one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other cells capable of being cultured in vitro as known in the art. The biological material also may include additional components to facilitate analysis, such as fluid (e.g., water), buffer, culture nutrients, salt, other reagents, dyes, etc. Accordingly, the biological material may include one or more cells disposed in a culture medium and/or another suitable fluid medium. As used herein the phrase, "Discs or plates" describes, but are not limited to, any geometrical shaped material capable of providing surface area for attachment, entrapment or encapsulation of particles like, but are not limited to, cells, proteins and other biochemical and chemical substances.

As used herein the phrase, "disposable" mean, but are not limited to, any process suitable material once used for the purpose essentially be discarded and not to be reused for the same of other purpose. As used herein, the term "disposable material or disposable film" refers to a polymeric films, including for example, multilayer polymeric films and thermoplastic film made using a film extrusion and/or foaming process, such as a cast film or blown film extrusion process. For the purposes of the present invention, the term includes nonporous films as well as microporous or macroporous films. Films may be vapor permeable or impermeable, and function as liquid barriers and/or gas barriers under normal use conditions. As used herein, the term "polymers" or "polymeric material" includes, but is not limited to, homopolymers, copolymers, such as for example, block, graft, random and alternating copolymers, terpolymers, etc and blends and modifications thereof. Furthermore, unless otherwise specifically limited, the term "polymer" shall include all possible geometrical configurations of the material. These configurations include, but are not limited to, isotactic, syndiotactic and atactic symmetries. The polymers used in the present invention can be natural, synthetic, biocompatible and/or biodegradable. The term "natural polymer" refers to any polymers that are naturally occurring, for example, silk, collagen-based materials, chitosan, hyaluronic acid and alginate. The term "synthetic polymer" means any polymers that are not found in nature, even if the polymers are made from naturally occurring biomaterials. Examples include, but are not limited to aliphatic polyesters, poly(amino acids), copoly(etheresters), polyalkylenes, oxalates, polyamids, tyrosine derived polycarbonates, poly (iminocarbonates), polyorthoesters, polyoxaesters, polyamidoesters, polyoxaesters containing amino groups, poly(anhydrides), polyphosphazenes and combinations thereof. The term "biocompatible polymer" refers to any polymer which when in contact with the cells, tissues or body fluid of an organism does not induce adverse effects such as immunological reactions and/or rejections and the like. The term "biodegradable polymer" refers to any polymer which can be degraded in the physiological environment such as by proteases. Examples of biodegradable polymers include, collagen, fibrin, hyaluronic acid, polylactic acid (PLA), polyglycolic acid (PGA), polycaprolactone (PCL), polydioxanone (PDO), trimethylene carbonate (TMC), polyethyleneglycol (PEG), alginate, chitosan or mixtures thereof.

The term "Suitable materials" include, but not limited to, e.g., films, polymers, thermoplastic polymers, homopolymers, copolymers, block copolymers, graft copolymers, random copolymers, alternating copolymers, terpolymers, metallocene polymers, nonwoven fabric, spunbonded fibers, meltblown fibers, polycellulose fibers, polyester fibers, polyurethane fibers, polyolefin fibers, polyamide fibers, cotton fibers, copolyester fibers, open cell foam, polyurethane, polyvinyl chloride, polyethylene, metals, alloys, fiberglass, glass, plastic (e.g., polyethylene (PE), polypropylene (PP), polyvinyl chloride (PVC), polyethylene terephtalate (PET), polyetheretherketone (PEEK) and polytetrafluoroethylene (PTFE) and polyfluoroalkoxy (PFA) derivates thereof), rubber, and combinations or mixtures thereof. Suitable rigid polymers include, but are not limited to; USP Class VI approved polycarbonate and polystyrene. Suitable flexible polymers include, but are not limited to, low density polyethylene and ethylene/vinyl acetate copolymer.

By "cell culture" or "culture" it means the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

By "cultivation" is meant the maintenance of cells in vitro under conditions favoring growth, differentiation or continued viability, in an active or quiescent state, of the cells. In this sense, "cultivation" may be used interchangeably with "cell culture" or any of its synonyms described above.

The phrases "nutrient medium", "cell culture medium" and "culture medium" refer to a nutritive solution for cultivating cells and may be used interchangeably.

The present invention provides a system, method and apparatus for handling of biological material and/or supporting large-scale culturing of biological cells, by propagating, culturing, entrapping or encapsulating cells or biological material directly on discs arranged in the support matrix contained within the culture vessel.

Now as shown in first embodiment illustrated in FIG. 1, the bioreactor system for culturing biological cells according to present invention mainly comprises, a culture vessel (1) being oriented horizontally and equipped with an inlet port (1a) for introducing nutrient (culture) medium and/or biological cells into and a outlet port (1b) for discharging the nutrient (culture) medium from the vessel (1), a support matrix (2) wherein the cultivation process take place being longitudinally disposed within the interior of the culture vessel (1) (shown in FIG. 1 (b)) and both end of which are rotatably fixed such that the nutrient medium is introduced through the inlet port (1a) within culture vessel and after flowing through the support matrix (2) being discharged through the outlet port (1b) from the culture vessel (1), a fluid pumping means (3) for driving the nutrient medium through the vessel (1), a gas exchange module (4) for dissolving gases into and removing waste gases from the nutrient medium and a main conduit (5) fluidly and externally connects said inlet port (1a) and outlet port (1b) to form a closed external loop (shown by arrow A) for circulation of nutrient medium and being extended through the gas exchange module (4) and fluid pumping means (3). Recirculation loop (A) essentially include silicon tubing, one or more fluid reservoirs, one or more pumping means, one or more gas exchange module (4) for effective mass transfer of gases between re-circulating fluid (nutrient fluid) and gaseous phase. It is within the scope of present invention to employ pressure indicator and regulator, kinetic energy sources for rotation of discs loaded within the support matrix and baffling means, one of more sensing elements, process control means, variable speed pump and/or fixed speed pump (not shown) in the fluid recirculation system. The nutrient fluid is discharged through the fluid outlet port (1b) and passes from the gas exchange means (4) through the fluid pumping means (3) and then fed into the culture vessel (1) through the inlet port (1a) to form a closed circulation loop (A) through the main conduit (5). Said gas exchange means (4) is capable of transferring oxygen into and removing carbon dioxide from the nutrient medium.

Preferably a short stretches of silicon tubing can be used as a main conduit (5) to connect the components of the recirculation loop and to the inlet and outlet of the culture vessel. These tubings allow free passage of fluid from within and transfer the fluid from one component to another. Silicon tubings of various lengths and diameters can be used depending on the scale of operation and the nature of the process application according to present invention.

In another embodiment of the invention as shown in FIGS. 2a and 2b, the bioreactor system mainly comprises a culture vessel (1) being oriented vertically and comprising an inlet port (1a), outlet port (1b), a support matrix (2) being longitudinally and substantially vertically disposed within the interior of the culture vessel (1) and both end of which are rotatably fixed such that the fluid is introduced through the inlet port (1a) within culture vessel and after flow through the support matrix (2) being discharged through the outlet port (1b) from the culture vessel (1) thereby to partially fill the vessel to create overlay headspace, a fluid pumping means (3), a gas exchange means (4) and a main conduit (5) fluidly and externally connects said inlet port (1a) and outlet port (1b) to form a closed external loop (shown by arrow A) for circulation of nutrient medium and being extended through the gas exchange module (4) and fluid pumping means (3).

Figure 4:
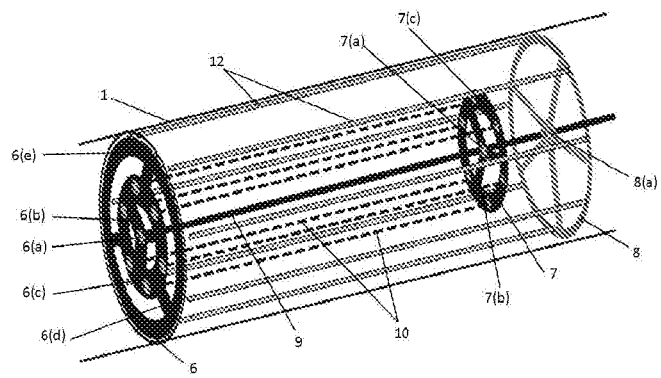
FIGS. 4a and 4b illustrates a detailed view of support frame work loaded within the support matrix according to present invention.
FIG. 4c illustrates a perspective view of the shaft driving mechanism according to present invention.
Figure 4:
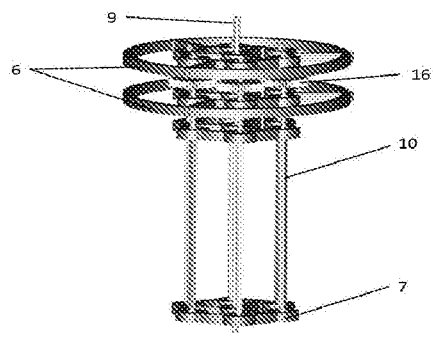
Figure 4:
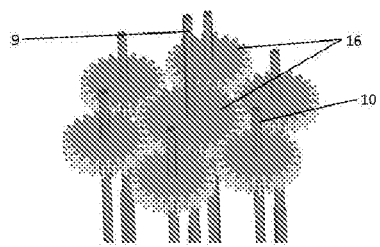
Figure 5:
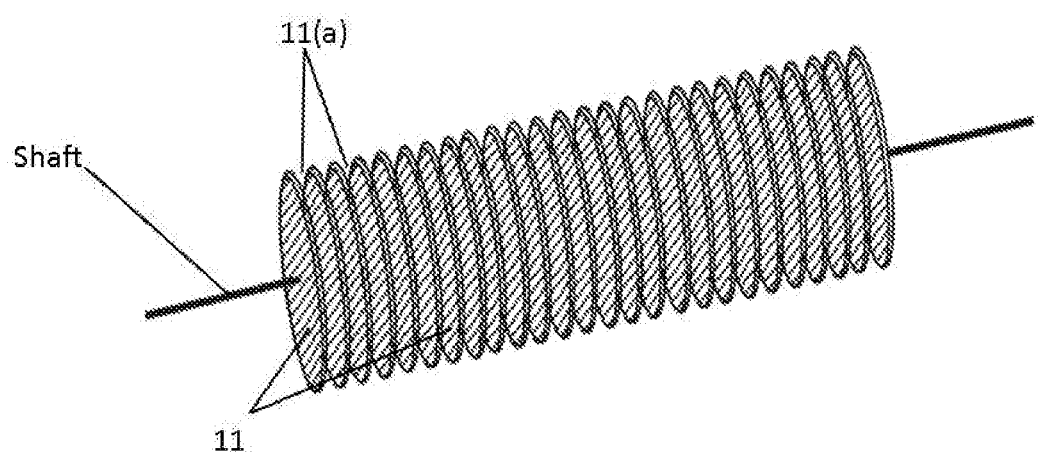
FIG. 5 illustrates an arrangement of discs loaded along length of the shaft according to present invention.
Figure 6:
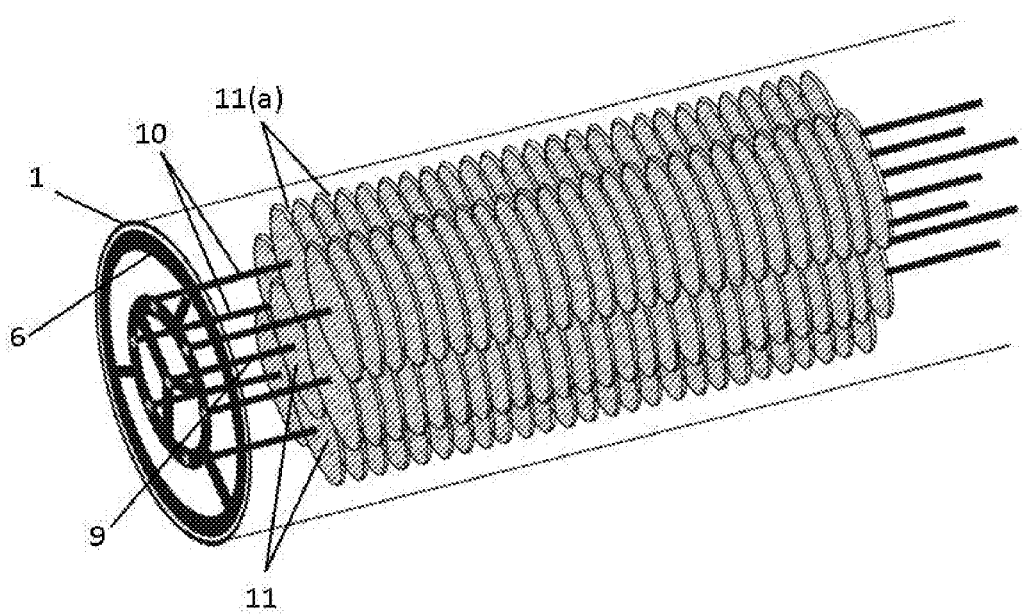
FIG. 6 illustrates an arrangement of central and peripheral shafts loaded with discs according to present invention.

Now as shown in FIG. 3 and FIGS. 4a to 4c, the support matrix (2) essentially comprises a support framework (6) having a hollow centre (6a) and spokes (6b) extended radially from the hollow centre (6a) to form an inner circular plate (6c) and spokes (6d) extended radially from the circular plate (6c) to form a baffle supporting frame (6e) having plurality of notches, said support framework (6) is rotatably secured with the internal wall of vessel (1) and located proximity to one end of said vessel (1), a shaft mounting frame (7) mounted preferably at the another end of said vessel (1) having a hollow centre (7a) and spokes (7b) extended radially from said hollow centre (7a) to define outer circular plate (7c), a baffle mounting plate (8) with hollow centre (8a) having diameter substantially similar to support framework (6) and rotatably located near to the shaft mounting frame (7), at least one rotatable central shaft (9) being axially extended from the hollow centre of the support framework (6), the shaft mounting frame (7) and baffle mounting plate (8), plurality of rotatable peripheral shafts (10) (shown by stippled lines) radially and parallelly mounted with respect to axis of the central shaft (9), each said peripheral shaft (10) is anchored at its both ends between the inner circular plate (6c) and the outer circular plate (7c) such that said plurality of peripheral shafts (10) radially surrounds the central shaft (9), plurality of spaced apart discs (11) longitudinally mounted along the length of said central shaft (9) and each peripheral shaft (10) (shown in FIGS. 5 and 6). Said support framework (6) having a suitable tensile strength and support the substantially low-friction rotation of the said shafts. The ends of the central shaft (9) are extended further through hollow centre towards the upstream and downstream end of the culture vessel (1).

Figure 8:
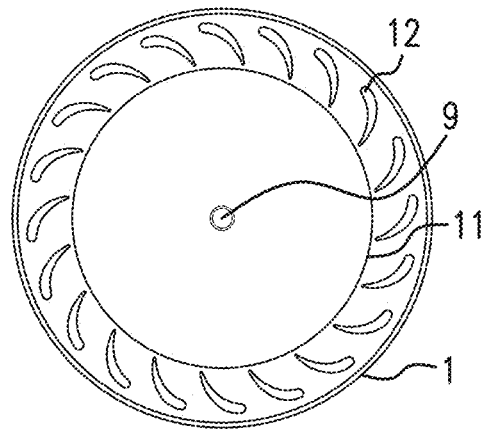
FIGS. 8a to 8f illustrates an arrangement of central and peripheral shafts in different geometries within the support matrix according to present invention.
Figure 8:
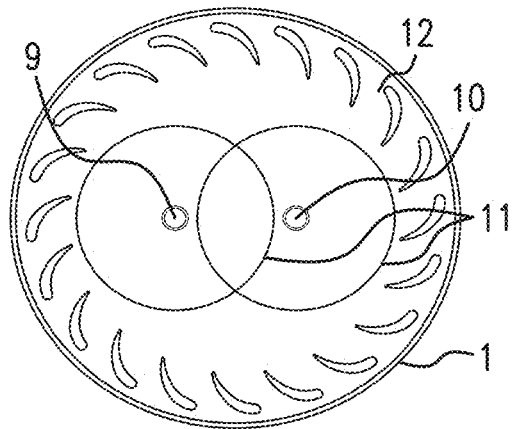
Figure 8:
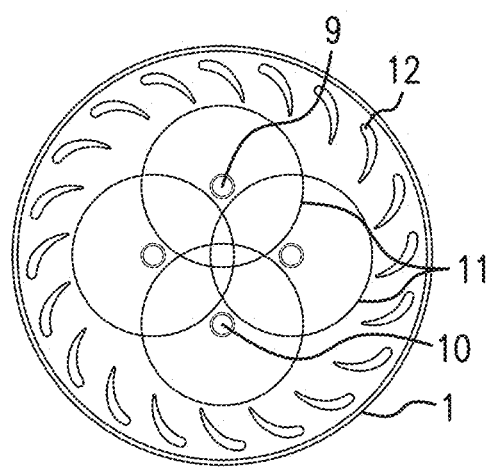
Figure 8:
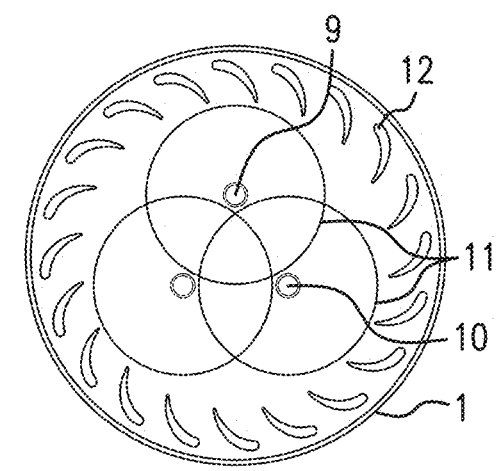
Figure 10:
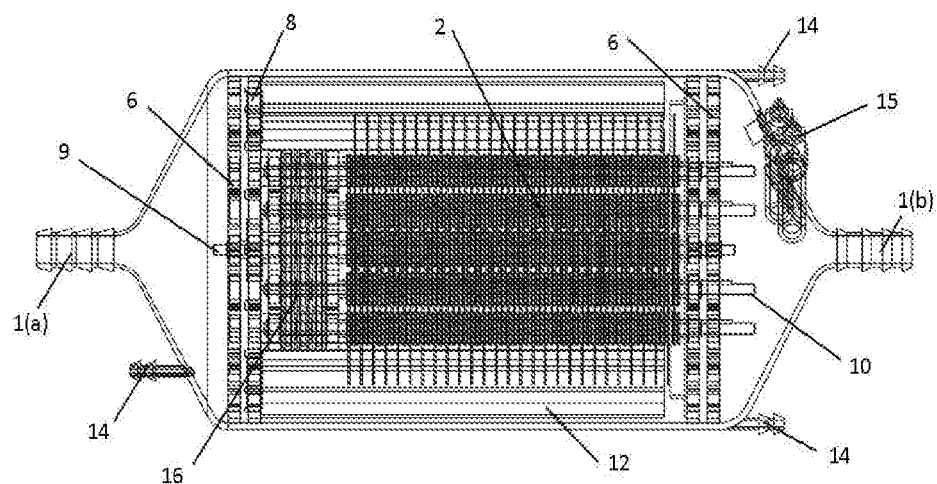
FIGS. 10a and 10b illustrates a detailed sectional view and perspective view of horizontally oriented support matrix and culture vessel with sensor elements according to present invention.
Figure 10B:
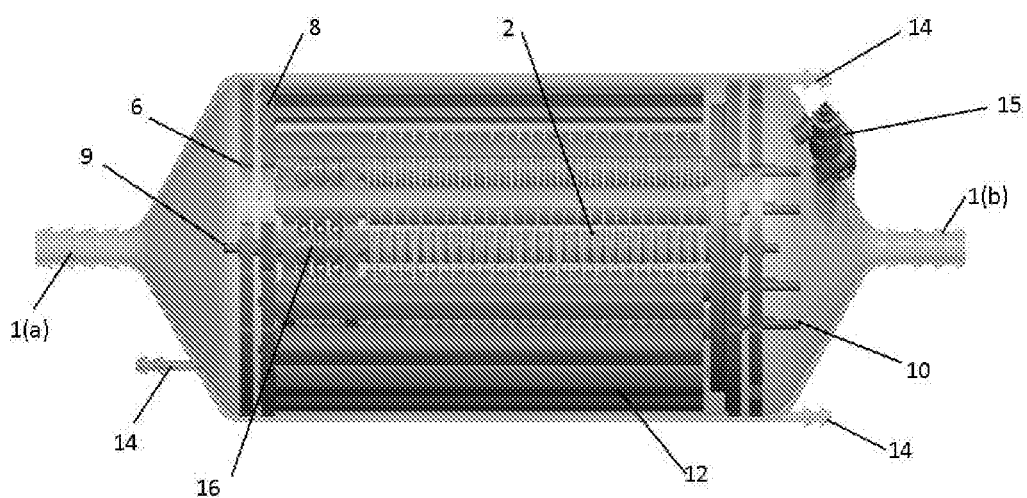

It is to be noted that in the preferred embodiment of the present invention, the system includes six co-axially arranged peripheral shafts (10) around the central shaft (9). However, it is within the scope of the invention that more or fewer peripheral shafts may also be mounted in different geometric arrangements as illustrated in FIG. 8.

Figure 3:
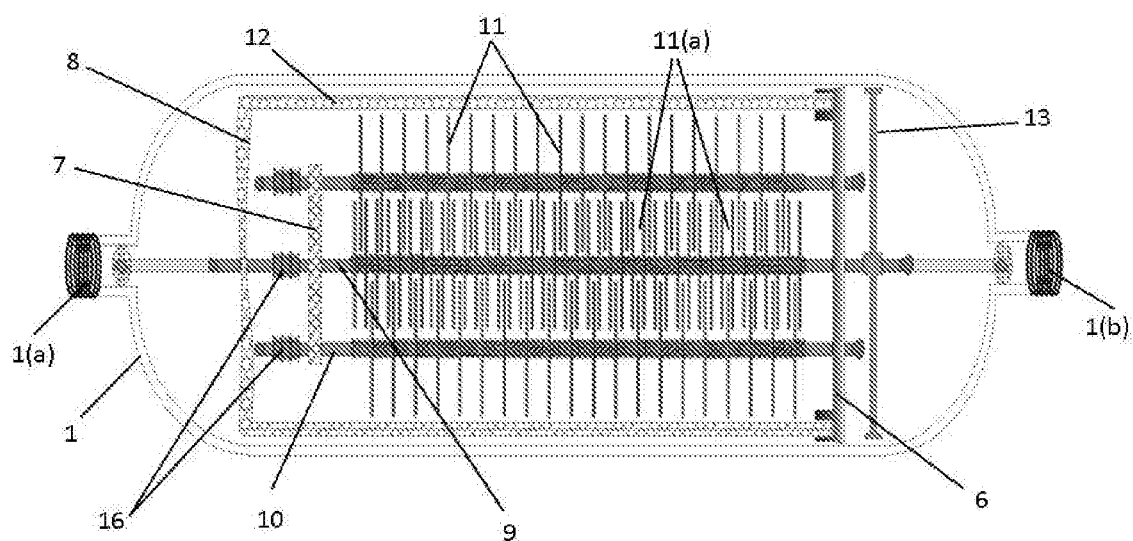
FIG. 3 illustrates a sectional view of culture vessel illustrated in FIG. 1 with support matrix loaded therein according to present invention.

Referring continuous with FIG. 3 and FIG. 4a, to enhance the mixing conditions within culture vessel (1), said support matrix (2) also comprises plurality of deflector vanes (baffling means) (12) that are extended along the axial length of the culture vessel (1) by radially surrounding the peripheral shafts (10). One end of each deflector vane (12) is molded on the baffle mounting plate (8) and another end of each vane (12) is received by its corresponding notches of the baffle supporting frame (6e) of support framework (6) at the opposite side, thereby substantially surrounds the plurality of peripheral shafts (10). The deflector vanes (12) are preferably angled substantially approximately 45° from the peri-centric outer surface of the baffle supporting frame (8). Rotation of said central shaft (9) and the peripheral shafts (10) causes the discs (11) mounted along the length of the shafts thereof and the baffle deflector vanes (12) to rotate. It is within the scope of present invention that in case when no peripheral shafts are located surrounding central shaft (9) then the central shaft discs (11) are directly surrounded by one or more deflector vanes as baffling means (shown in FIG. 8a).

The culture vessel (1) according to preferred embodiment is preferably in a shape of a closed cylindrical container that substantially encloses the support matrix (2). While illustrated as generally cylindrical in shape, the shape of the culture vessel (1) is not so limited, as vessels of various shapes (e.g., parallelepiped) may be provided. Essentially, the culture vessel of the present invention serves as culture chamber, cylindrical, rectangular or any other shape capable of easy handling. While in operation, the culture vessel can be preferably oriented along the horizontal axis however the vertical and other axial orientations can be best suited according to the process demands as discussed later. Though in given embodiments, the support matrix (2) is substantially enclosed by the vessel (1), however, it is within the scope of present invention to partially cover said support matrix (2) by culture vessel (1). Further, it is also within the scope of present invention to utilize the support matrix (2) which is not covered or not contained within the culture vessel (1).

The bioreactor system according to present invention preferably in disposable format as sterile single-use bioreactors manufactured from polymeric suitable materials, such as fluoropolymers, high density polypropylene (HDPE) and specially-treated polystyrene plastics. In certain embodiments, one or more parts of the system may be made of glass, stainless steel and/or other biocompatible material.

Further, the culture vessel (1) according to present invention is preferably made from a large variety of suitable materials which are capable of withstanding sterilization techniques, including, but not limited to, plastic, metal, glass, ceramic and the like. The diameter and length of culture vessel is dictated by process conditions and scale. The culture vessel, support matrix and other culture contact parts according to present invention are preferably manufactured from pyrogen free and sterilizable materials, to reduce risks associated with cross contamination.

In a preferred embodiment, a disposable culture vessel (1) is manufactured from rigid plastic material which is substantially or fully transparent to allow for visual inspection of the vessel contents before and after use and to explore the internal in-process conditions when the bioreactor is in operation. All valve and conduit attachments are sealed and filtered to keep the entire vessel air/liquid tight and leak proof. Various panels of the vessel are sealed to each other to form air-tight and water-tight seams by plastic film sealing techniques using heat, high radio frequency or other techniques. Then, the connectors, tubing, filters and closures are attached to the vessel to create the sterility barrier. The assembled vessel then can be sterilized by, for example, exposing the individual culture vessel to gamma irradiation, preferably between 25 to 50 K gray. Suitable materials for constructing the disposable culture vessel include multi-layered or single-layered plastic films, including films made of polyethylene or Polyvinylidene Fluoride (PVDF) with desired thickness according to the process suitability. Alternatively, the vessel may comprise a relatively rigid container that is, for example, formed by injection molding a suitable plastic, such as Polyethylene Terepthalate Glycol (PETG) or polycarbonate and which may or may not be supported by auxiliary structures.

In another embodiment, the culture vessel (1) is preferably made of multilayer rigid plastic material and the inner side of the vessel wall is constructed with a gas permeable membrane/material or tubing patches sealed within the vessel body and thereby additional source of gas exchange and mass transfer can be incorporated when the bioreactor is in operation. The wall of disposable plastic vessel may comprise a multilayer laminate structure. A plurality of layers of different materials may be laminated together to provide a desired function. One or more gas barrier layers formed of a material such as ethylene vinyl alcohol (EVOH) can be included. Tie layers may be provided between different layers of materials. The material selection is based on obtaining sufficient strength for the wall of vessel to hold the volume of fluid and content to be filled in within the culture vessel. One or more air gaps having bonded or un-bonded regions may be provided in a multilayer or composite rigid film. The air gap channels thereby created/molded within the vessel wall extends along the length of the cylindrical wall of the vessel covering the support matrix. These air gap channels are collectively connected to gas inlet for bringing gases like air, oxygen, carbon dioxide, nitrogen etc. to bioreactor and a gas outlet for removing the gases like carbon dioxide produced by the microorganisms or cells. Flow of desired gases from the air gap channels of vessel wall provide additional means for mass transfer between fluid within the culture vessel and gases. A preferred multilayer laminate includes a polyamide outer layer, a first tie layer, a polyethylene or polyethylene blend/copolymer layer, a second tie layer, an EVOH (gas barrier) layer, a third tie layer, another polyethylene or polyethylene blend/copolymer layer, an air gap, and then an inner contact layer comprising gas permeable polyethylene or polyethylene blend/copolymer layer including silicon membranes.

Also according to another embodiment, culture vessel (1) can be made of, but not limited to, glass, or any other chemically non-reactive, biocompatible material like ceramic, stainless steel and the like. In case where the culture vessel is to be used as non-disposable vessel, the support matrix (2) can be assembled in-place manually or with the use of automated machines. Preferably, one of more part of the support matrix can be disposable. After enclosing the support matrix and assembling the culture vessel, the bioreactor system can be sterilized by any suitable sterilization method preferably steam sterilization. Alternatively, the support matrix enclosed within the culture vessel can be in pre-packed disposable format wherein the support matrix with flexible outer cover can be disposed within a non-disposable culture vessel. In this case, outer covering of support matrix serves as an isolation barrier and made of any suitable type of any stretchable, collapsible, pliable and/or elastic material and the culture vessel serves as a support container which may be manufactured from suitable material.

Figure 2:
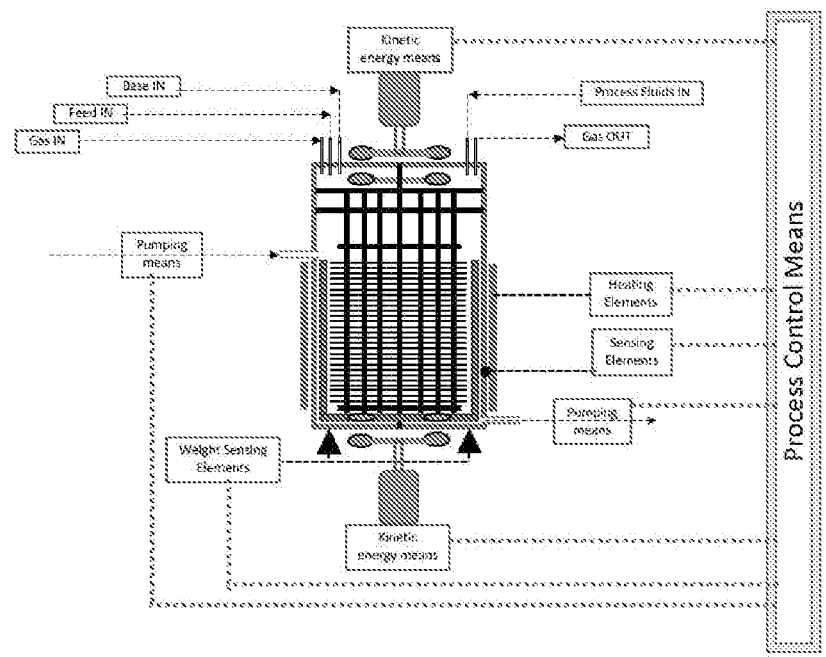
FIG. 2a illustrates a schematic representation of bioreactor system with vertically oriented culture vessel according to present invention.
FIG. 2b illustrates a schematic representation of bioreactor system with vertically oriented culture vessel and recirculation loop with gas exchange means.
Figure 2:
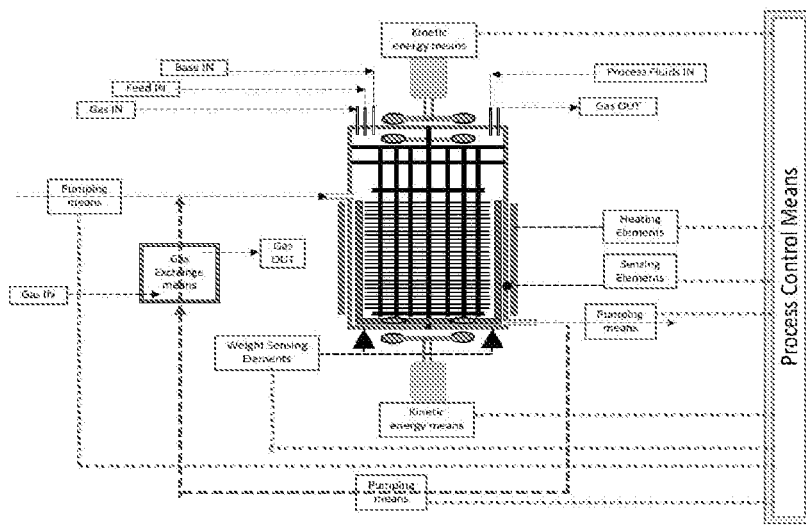

As illustrated in FIGS. 2a and 2b, to gain the rotational motion, the central shaft (9) is mechanically coupled to receive kinetic energy from a kinetic energy source (19). Here, one or more magnetic rotation means (13) for shaft rotation and one or more magnetic rotation means for baffling means rotation is employed to receive kinetic energy from external kinetic energy source as shown in FIG. 2. However, said source for kinetic energy includes, but not limited to, a mechanical seal with motor, one or more servos, pistons, solenoids, linear or rotary actuators and external electromagnetic or magnetic means, or the like. To facilitate the smooth rotation of the loaded shafts, means to reduce the frictional forces in form of bearings (not shown) are mounted on the support framework (6) at the junction of the shaft ends and framework (6).

Said magnetic rotation means (13) comprises an internal magnet (not shown) that is fixedly connected to at least one end of the rotatable central shaft as shown in FIGS. 2 and 3. The internal magnet is rotated by magnetic force exerted by external magnetic mechanism, preferably. Thus, the rotation of an external magnet which, in turn, causes internal magnet and thereby rotatable shaft to rotate. An electrically operated magnetic rotation means covering the small patch of the vessel externally can be implanted to give magnetic acceleration to internal magnet. This magnetic rotation means eliminates the use of mechanical seal and thereby offers the additional level of safety from extraneous contamination sources. In another embodiment of rotating means, the central shaft (9) is directly connected to a motor located outside of bioreactor via a motor shaft. A shaft of motor invades the vessel wall using mechanical seal device and transmission system is employed to connect the central shaft with the shaft of motor. Other mechanisms or combinations of mechanisms can be employed as per the suitability of the process and economics.

Now FIG. 5 shows an arrangement of disc on the central shaft (9) and the peripheral shaft (10). According to FIG. 5, the (permeable) discs (11) are centrally and longitudinally mounted on each shaft by maintaining predetermined space between two successive discs (11) through a spacer (not shown) to define an interspatial space (11a). Said spacer disposed between the discs maintains substantially equidistant separation between the discs (11). Preferably spacers can be made of a similar material which is used for the construction of discs (11) or spacers can be made of silicon rubber. Ratio of spacer diameter and disc diameter is to be optimized according to the process scale. Additionally, as described in FIG. 11 (b), other means of supporting and separating the discs may be employed; for example, but not limited to, each disc have a ridge or spacer formed integrally during its construction at the central portion. This ridge or spacer then rests on the spacers of the discs immediately adjacent to it. The presence of cylindrical spacers between each disc essentially ensures that the discs mounted on a shaft are in a separated state throughout the operation. To maximize the disc loading capacity of bioreactor and to achieve desired compactness of the support matrix, the ratio of diameter of discs loaded on central shaft to the diameter of discs loaded on peripheral shafts can be adjusted. Preferably, the diameter of discs loaded on central shafts is larger than the diameter of the discs mounted on peripheral shafts to maximize the intermingling of the discs and to efficiently occupy the interspatial space created between central shaft discs by the discs loaded on peripheral shafts.

FIG. 6 depicts the arrangement of the disc loaded on the peripheral shafts (10) and the central shaft (11) within the support matrix (2). From FIG. 6, it is seen that the portion of each disc (11) loaded on each peripheral shaft is partially extended into the interspatial space (11a) of the disc loaded on the central shaft (9).

Figure 11:
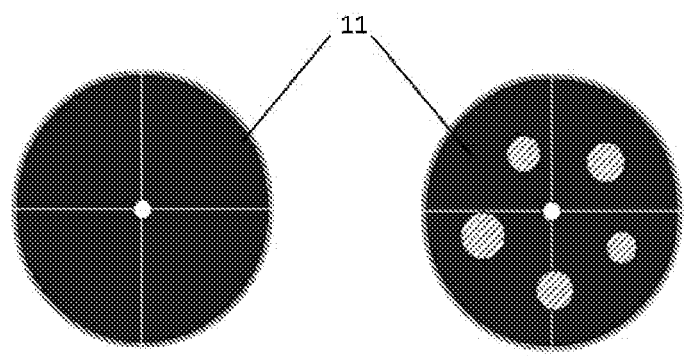
FIGS. 11a and 11b illustrates a sectional view and geometrical arrangement of discs to be loaded on the shafts.
Figure 11:
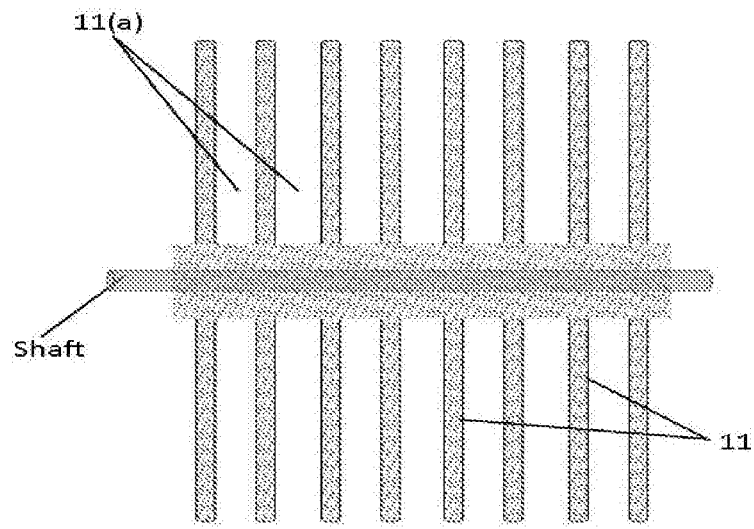
Figure 12:
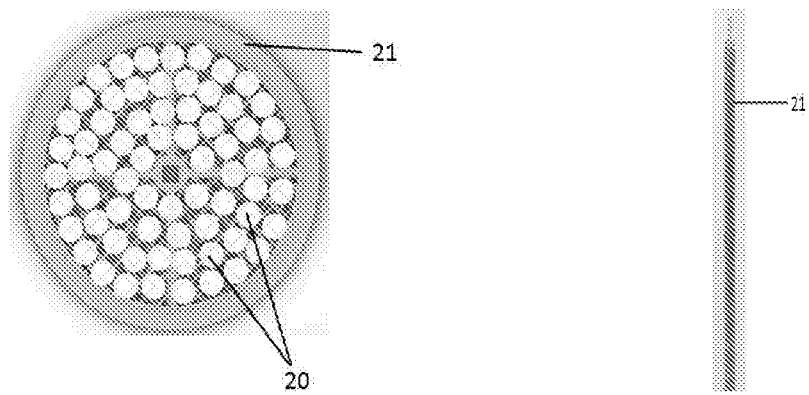
FIGS. 12a, 12b, 12c and 12d illustrates use of commercially available cell carriers in discs' form according to present invention.
Figure 12:
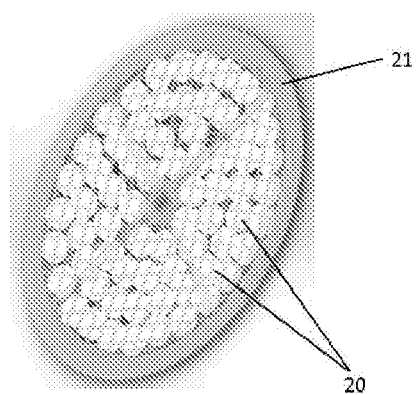
Figure 12:
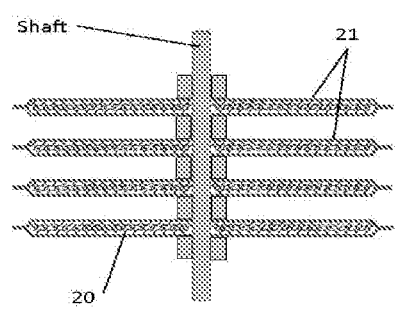

The discs (11) according to present invention are preferably constructed from, but not limited to, a non-woven fibrous material. FIG. 11 illustrates the geometry of discs or plates (11) essentially provide the required substratum for cell attachment and growth thereafter. Cellular attachment can occur on either side of the disc, thereby providing a very large surface area for attachment and growth of cells within a small space or volume. Typically, a thin monolayer or film of the cell growth is observed on disc surfaces and generally has a thickness of from a few µm, e.g. 1 µm, to about 1 mm, i.e. 100 µm. In case of where applications demand for multilayered or structured growth of cells, the discs (11) are molded in desired shape and the surfaces can be created by treating them physically, chemically or biologically.

In another embodiment as described in FIGS. 12a to 12d, commercially available cell carriers (20) for example Fibra-Cel discs and BioNOC-II carriers can be used wherein the carrier material was placed or filled between fluid permeable molded disc frames (21). After packing of commercial cell carriers of variety of size and shapes, disc frames can be fixed on central shaft and peripheral shafts.

FIG. 11 illustrates another embodiment of geometry for discs (11) constructed from porous and fibrous non-woven mass of plastic material preferably polyester fibers with polystyrene or polypropylene support and alternatively discs surfaces can be coated with macro or micro carriers. In this case, any open-to-cell plastic matrix can be used. Care must be taken in the formation of the plastic matrix that it is sufficiently porous not only to allow the flow of the liquid nutrient medium through its interstices, but also porous enough to allow the free passage of cells. Otherwise, difficulty can be encountered in homogeneous cell spreading and subsequent growth of cells or in harvesting cells. Discs (11) can have any suitable pore size and geometry and are, in addition, modified by the inclusion of various structures, such as a polymer coating or microbeads, onto the surfaces. Alternatively, or additionally, some or all of the surfaces of discs are chemically or biologically modified or treated, so as to enhance overall process effectiveness. Pore sizes of the disc material may vary according to the process demand. Perforations can be provided, however. In an alternative embodiment, holes or apertures created on the discs to enhance the mixing conditions within support matrix. Pattern, shape, size and diameter of these holes increase the scale of turbulence by creating flow pattern which prevents the stagnant non-homogeneous area between the closely stacked discs.

Further, said culture vessel (1) according to present invention preferably comprise one or more conduits for entrance of the biological material including cells, culture media, and other feeds and at least one conduits for removal of waste metabolites and spent media.

Now according to FIG. 9, additionally said culture vessel (1) is configured to receive medium addition and outlet. conduit, a base addition conduit, a sampling line, an inoculum/seed addition line, and a line for nutrient feed medium addition and air vents as shown by numerals (14). Although conduits are shown as disposed at particular position in the walls of culture vessel (1) in FIG. 9, they can be disposed at any desired location on vessel that will cause the fluid to enter and leave the culture vessel and thereby culture system receives homogeneous nutrient and gas distribution to enhance growth of organisms grown on the surface of the support matrix (2). Said conduits are made of suitable material preferably from material which is used for the construction of culture vessel (1).

Culture vessel (1) also comprise one or more ports for filling, spiking, aerating, adding and/or draining components to reduce the amount of human contact with the various components (which may be hazardous, dangerous and/or infectious) that are to be mixed as part of and during the mixing of such components. Suitable ports nonexclusively include any sanitary leak poof fittings known in the art such as compression, standard in-gold or sanitary type fittings. Suitable joints nonexclusively include pipes, tubes, hoses, hollow joint assemblies, and the like. Additionally, vessel can preferably be equipped with one or more of input ports for process feedstock inputs (e.g.: pH buffers, glucose etc.).

The bioreactor system according to present invention is suitably equipped with one or more sensing elements preferably pre-inserted and pre-calibrated sensors to measure temperature, dissolved oxygen, pH, dissolved carbon dioxide, metabolites and the like within the culture vessel (1). These sensors are either traditional electrochemical sensors and/or disposable and pre-calibrated optical sensors. The culture Vessel (1) thereby comprise one or more probe openings (15) (see FIG. 9, 10*a*, 10*b*) for sensors to measure the pH or/and dissolved oxygen and the like. In the preferred embodiment, one or more dissolved oxygen probe and pH probe are used which extend into the interstices of the culture vessel. One or more vent port with vent filter is also provided for escape of air initially present in the culture vessel at the time of filling and harvesting the culture vessel.

Further, to maintain a substantially fixed liquid volume in bioreactor, culture system may further include a load cell for accurate mass balance maintenance and/or overflow outlet which may be in the form of a pipe extending outward from the vessel so that the portion of the vessel content can be withdrawn to maintain desired liquid level. It is essential to maintain constant volume of nutrient media or fluid for steady state environment and to enable the perfusion processes for the bioreactor system.

To maximize the efficiency of the system according to present invention, it is desirable to tightly control the process temperature. This can be accomplished in a number of ways, one of which involves the use of one or more heating blankets. Alternatively, water jacket system can be provided as part of culture vessel wall. Vessel wall thereby includes a water jacket surrounding the length of the vessel and an inlet and outlet conduits for temperature regulating fluid flow through the water jacket. Alternatively, to maintain desired temperature of the culture system, the vessel can be kept/located within the temperature controlled area like inside an incubator room.

Figure 13:
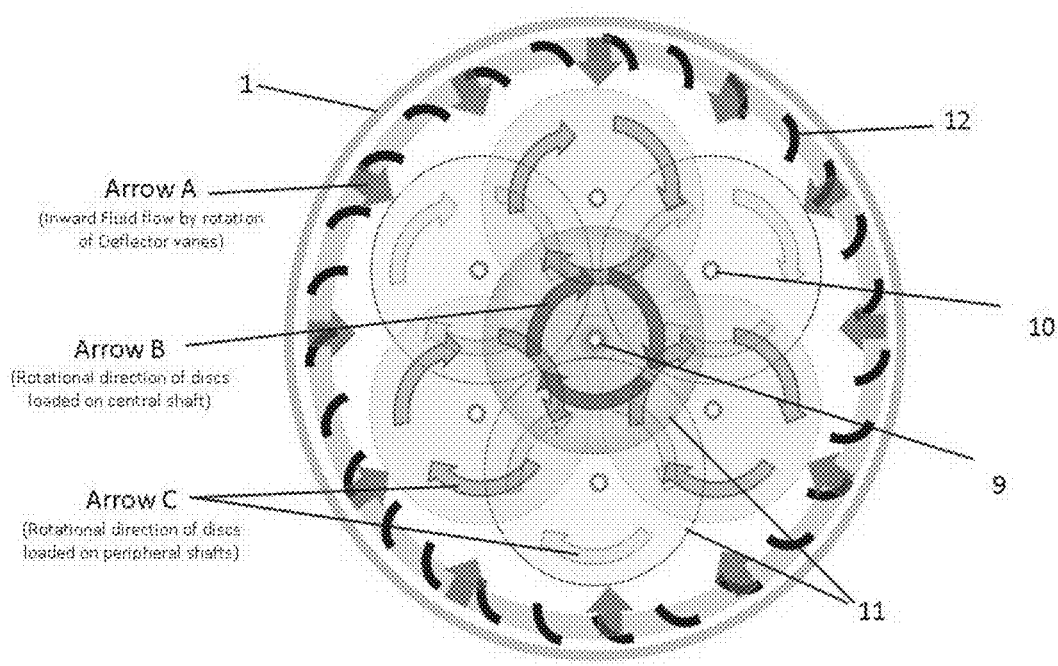
FIG. 13 illustrates rotational pattern and directions of rotation of the discs loaded on the central and peripheral shafts according to present invention.

Referring FIGS. 3, 6 and 13, the arrangement of peripheral shafts (10) around the central shaft (9) is such that discs (11) of the peripheral shaft (10) while rotating, invade the space created between the discs (11) of the central shaft (9). As explained in FIG. 13, when six peripheral shafts (10) surround central shaft (9), at a time in one geometric plane, the discs loaded on three alternate peripheral shafts invade the interspatial space created between two successive discs of central shaft. The interspatial rotation of the peripheral discs (11) from the vicinity or space between the successive discs (11) (interspatial space) of central shaft (9) create a flow path of the biological material or fluid that ensures sufficient mixing and avoid the stagnant fluidic zones which can be created when the discs are mounted closely apart from each other on the shafts. The fluid flow pattern produced by rotation of discs (11) from central (9) and peripheral shafts (10) makes the bioreactor system more efficient and capable of supporting high cell densities then the other conventional cell culture systems since all the prior art disclosed system suffer form the problem of non-homogeneous condition within the matrix bed and observed to gain inefficient mixing for nutrient distribution and mass transfer.

As depicted in FIGS. 3 and 4, in present invention, to connect and rotate the peripheral shafts (10) with rotation of central shaft (9), preferably, the shaft drive mechanism (16) like timing belt and pulley system or gear drive system (as illustrated in FIG. 4 (*c*)) is used. In the preferred embodiment, the timing belt and pulley system is used wherein the driver pulley is located fixedly on central shaft and driven pulleys are fixed on peripheral shafts. Other drive mechanism like friction system, Spur system, chain and sprocket system can be used to drive the peripheral shafts (10) along with central shaft (9). In Shaft driving systems employed herewith, rotational speed of peripheral shafts with respect to central shaft can be changed by varying the diameter of pulley or gear plates.

In another embodiment of the invention, plurality of shaft mounting frame (7) is used to maintain the peripheral shafts stationary at their fixed location on the framework. Shaft driving mechanism (16) is installed in-between the plurality of shaft mounting frame (7). Further, another support framework (6) is mounted fixedly to the vessel wall at the opposite and distal end of the vessel relative to the prior installed support framework (6).

The arrangement, scaling and geometrical parameters for distance of peripheral shafts (10) from central shaft (9), diameter and thickness of discs, peri-centric diameter of deflector vanes etc are dictated by process scale and conditions. It is being apparent that, as explained, one or more peripheral shafts may also be mounted in different geometric arrangements and the edges of the discs extend to the interspatial area of the discs mounted on the other shaft as shown in FIG. 8. In another embodiment however one shafts can be arranged in support matrix (2) which is surrounded by rotating baffling means.

As illustrated in FIGS. 6, 7, 11 and 13, fluid flow directed inward by the radial deflector vanes (12) will impinge upon the discs (11) mounted on the shafts. In case of multiple shafts mounted in the support matrix as illustrated in FIG. 3, the discs (11) mounted on the peripheral shafts (10) first impinged by the inward fluid flow created by the rotary deflector vanes (12). Thus, discs (11) on the central shaft (9) receive replenished and fresh nutrient rich fluid current when the intermingled discs (11) of the peripheral shafts (10) rotates from the interspatial space of the central shaft discs (11).

Figure 7:
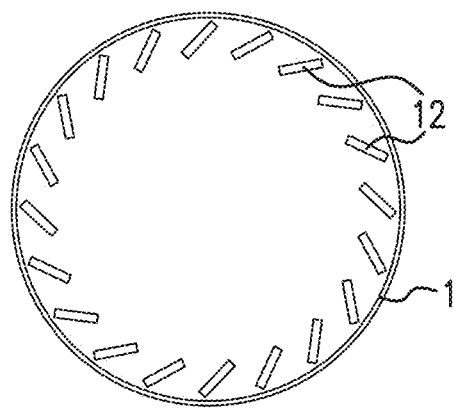
FIGS. 7a and 7b illustrates an arrangement of deflector vanes in different geometrical shapes surrounding central and peripheral shafts within the support matrix according to present invention.
Figure 7:
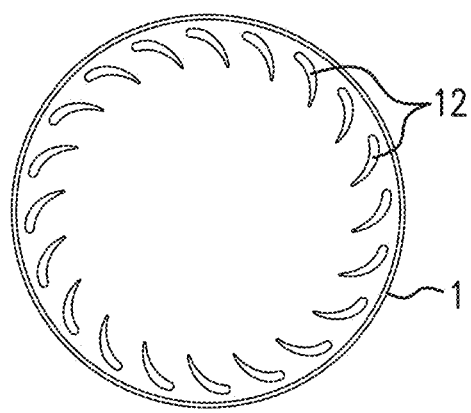
Figure 14:
FIGS. 14a and 14b illustrates a detailed view of arrangement of linear and twisted deflector vanes in the support matrix according to present invention.
FIG. 14c illustrates a perspective view of twisted deflector vanes with baffle mounting ring and contains impeller vanes.
Figure 14:
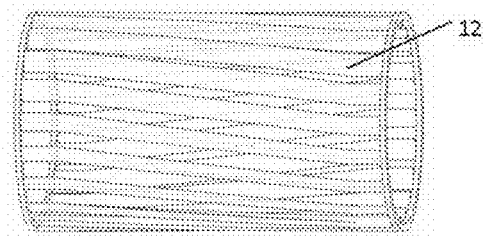
Figure 14:
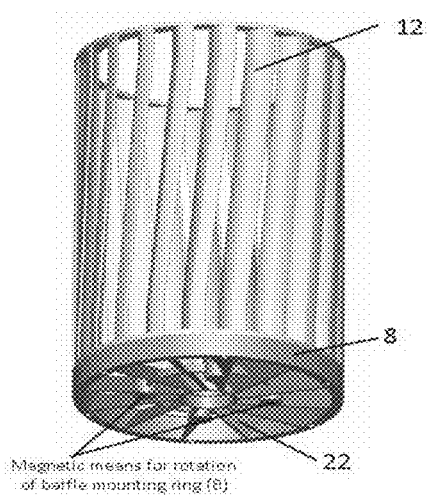

As illustrated in FIG. 7, it is to be noted that the size and shape of the deflector vanes (12) can be customized to generate different flow patterns, depending on the desired application. The deflector vanes may be substantially flat as shown in FIG. 7(*a*), for maximum tangential fluid flow in inward direction, or curved, and/or angled as shown in FIG. 7(*b*) to provide additional degree and intensity of inward flow. When the baffle mounting plate (8) rotates, the drag of the fluid generated by rotation of deflector vanes (12) creates necessary inward flow of fluid required to create homogeneous condition within support matrix. This inward motion of the fluid quickly achieves significantly lower mixing time when the deflector vanes (12) are twisted to certain degree and the baffle mounting ring (8) is constructed to contain impeller vanes As described in FIG. 14 (*c*), in vertically oriented vessels, the deflector vanes (12) are mounted on a baffle mounting ring (8) having radially disposed impeller vanes (22) to create upward flow towards the axial direction of the vessel whereby the radially disposed impeller vanes (22) prevent the settlement of the biological material, biological cells, debris and other suspended particles at the bottom of the vessel due to gravitational force. The rotation of the impeller vanes (22) along with the deflector vanes (12) can significantly improve the mixing conditions within vertically oriented culture vessel. FIG. 14 depicts the straight arrangement of defector vanes (12) in baffling means (shown in FIG. 14(*a*)), twisted arrangement of deflector vanes (12) (shown in FIG. 14 (*b*)) and baffling means with impeller vanes (22) mounted within baffle mounting plate (8) (shown in FIG. 14 (*c*)). These arrangements ensure that every location of the support matrix is substantially equivalent with respect to nutrient distribution whereby nutrient rich fluid flow through the interspatial vicinities of the discs and also ensure sufficient exchange of air or gases within support matrix.

It is within the scope of present invention to provide spiral shaped deflector vanes (12) on baffling means that are loaded fixedly on the central shaft (9) so that the rotational energy for baffling means is gained from flow of fluid flowing from one end to other end of the vessel (1) and the rotation of baffling means causes the central and peripheral shafts to rotate without external rotation means. Hence, without employing any rotating means, the bioreactor system according to present invention is operated.

In the preferred embodiment, rotation of the discs (11) and rotary deflector vanes (12) is mechanically coupled to receive kinetic energy from a kinetic energy source. Thereby, the rotation on the discs (11) and the deflector vanes (12) is controlled simultaneously. When the internal magnets (not shown) are mounted on magnetic arm fixedly mounted on central shaft, outside magnet is driven by mechanical mean i.e. motor belts. Motion of the outer magnet drive keep the internal magnets in motion and thereby give rotational motion for the shafts, discs (11) and deflector vanes (12) simultaneously at a controlled speed. Rotational means discussed herein may also include a mechanism for monitoring the speed of rotation of the discs and deflector vanes.

In another preferred embodiment, separate magnetic rotation means are used for discs (11) and for deflector vanes (12). Magnetic rotation means for discs' rotation is mounted fixedly on central shaft and the rotational means for deflector vanes are mounted on baffle mounting plate. In case where separate rotation means used for disc rotation and deflector rotation, the speed of rotation of discs and the deflector vanes rotation can be controlled and measured independently.

In the preferred embodiment of the present invention shown in FIGS. 1 and 2 because the discs are equally spaced apart, the flow of liquid culture medium over each plate is substantially uniform throughout reservoir when discs containing part of the support matrix is completely filled by a medium. Uniform flow through the reservoir can readily be proven by hydrostatic principles and uniform flow across all the plates can be empirically demonstrated by dye dispersion experiments.

In case of use in tissue engineering applications, suitable materials for discs construction may also include but are not limited to natural vegetable sponge, or animal sponges. Synthetic sponges made from polyurethane or other synthetic materials which meet the above criteria may be utilized. Such fibrous fabrics, having an average fiber diameter in the micrometer or nanometer scale, have been used to fabricate complex three-dimensional scaffolds for use in tissue engineering applications. These 2D and/or 3D scaffolds can be used in support matrix construction.

During Operation, the nutrient medium is filled into the vessel through the medium addition conduit. After proper conditioning of nutrient medium, the biological material is added within the vessel (1). Then said central shaft (9) and peripheral shafts (10) and deflector vanes (12) are rotated at certain rotating speed by providing kinetic energy through the magnetic rotation means (13). Process related physiological parameters are then controlled with the use of sensor elements and addition conduits with pumping means. Here, it should be noted that the central shaft (9) and the peripheral shaft (10) and deflector vanes (12) may be caused to rotate at different speed by employing separate rotating means. The interspatial rotation of the peripheral discs (11) from the interspatial space (11*a*) between the successive discs (11) of central shaft (9) creates a fluid flow pattern of the biological material or fluid that ensures sufficient mixing and avoids the stagnant fluidic zones which can be created when the discs are mounted closely apart from each other on the shaft. The fluid flow pattern produced by rotation of discs (11) from central shaft (9) and peripheral shafts (10) makes the bioreactor system according to present invention more efficient and capable of supporting high cell densities then the other conventional cell culture systems since all the prior art disclosed system suffer from the problem of non-homogeneous condition within the matrix bed and observed to gain inefficient mixing for nutrient distribution and mass transfer. Said pattern of arrangement of discs rotation ensures the absence of non-homogeneous and stagnant fluidic zones in the interspatial vicinities (space) (11*a*) between each disc. Further, such arrangement of disc rotation not only contributes to highly efficient mixing, but, as a further important advantage, facilitates the draining of the vessel contents on emptying, decanting or harvesting. Normally medium tends to be held between the plates by capillary action, but it has been found that when the plates are intermingling and rotated, draining efficiency is improved. For perfusion processing, calculated amount of fluid volume is continuously been drained out and fresh nutrient rich medium or fluids are being added in the vessel to maintain constant fluid volume and to achieve steady state equilibrium of the process. Once desired amount of product is produced, the vessel content is decanted or harvested and stored for further processing.

It is within the scope of present invention to utilize a vibrating tool or sonication probe inserted into the support matrix through culture vessel wall to effectively apply vibrating motion to the surfaces of the support matrix thereby to detach the biological cells adhered on discs' surfaces or active ingredient or particles coated on the surface of the support matrix discs.

Thus, the efficient mixing of the vessel contents according to the present invention ensures that a homogeneous system is achieved and maintained within the vessel. This efficient mixing result in rapid and complete distribution of constituents added to the vessel contents and ensures that continuous and reliable measurements of the composition and other conditions of the growth medium may easily be taken, as a result accurate process control by full instrumentation is made possible. The speed of and degree of mixing within the vessel is dependent on a combination of speed of rotation of the disc stack and the provision of auxiliary pumping means. Mixing may also further be improved by the increasing rotational speed of the baffling means and by adjusting the angling of the curved vanes. The influence and inter-relationship of speed of rotation of the stack of discs and the degree of auxiliary pumping of the vessel contents may be demonstrated by injecting into the culture vessel a quantity of dye, rotating the disc stack, effecting auxiliary pumping and determining the time taken for 95% dispersion of the dye throughout the vessel contents. The optimal patterning (e.g., size, shape and frequency) of discs, baffle vanes and peripheral shafts will be a function of the size of the reactor (scale), the velocity, viscosity, and nature of cell platform and its associated optimized growth medium. The particular patterning which provides optimal mixing condition can be determined through finite element analysis studies (www.fluent.com) or through empirical experiment. These studies generally include mixing studies as a function of time or number of agitation cycles.

Further, to enable each disc (11) to provide the maximum growth surface possible, the space between each plate and space between outer peripheries of discs (11) loaded on the peripheral shafts (10) and internal wall of culture vessel can be optimized and it is dictated by process conditions and scale.

One or more reservoir for holding the process fluids or nutrient medium is connected to the recirculation loop system, preferably, before the inlet of the culture vessel.

Further, in the preferred embodiment, the invention also utilizes a means for recirculation of medium via a pumping connector body, such as a vane pump, diaphragm pump or peristaltic pump or any other means of creating flow. It is within the scope of present invention to provide a recirculation system having a partial recirculation component in order to perfuse the bioreactor system with fresh nutrients.

Another key feature of bioreactor according to present invention is their ability to be linked in sequence, connecting the output of one bioreactor apparatus to the input of the next larger bioreactor apparatus. This sequential size of bioreactors allows use of the disposable bioreactors for the entire seed train as well as the production stage.

When scaling up from small units to large units, the device of the present invention is directly or linearly scalable such that gas exchange diffusion rates are maintained by simply increasing or incorporating more gas exchange membranes or tunings in gas exchange module or in culture vessel wall. The scaling up is accomplished by maintaining the thickness and height of the support matrix and the corresponding size of the culture chamber, and by expanding the support matrix to a useful production size. The aspect ratio (height vs. diameter of the vessel) and size of the support matrix with respect of culture vessel can be optimized and it is process dependent. Linear scalability reduces manufacturing development time, significantly reducing development costs and time-to-market.

The features or operations of embodiments of the present invention are performed by specific hardware components, which contain hard-wired logic for performing the operations, or by any combination of programmed data processing components and specific hardware components. Embodiments of the invention may be implemented with or include software, data processing hardware, data processing system-implemented methods, and various processing operations as described herein.

Now, FIGS. 15a, 15b and 15c depicts another embodiment of bioreactor system according to present invention. In this embodiment, as detailed in FIG. 15 (a), a vessel (1) and support matrix (2) is oriented in vertical configuration. It is to be noted that all components and their function and entire operation of the bioreactor system will be performed in the same manner as described in aforesaid embodiment with reference to FIGS. 1 to 14. In said embodiment, the vessel (1) is partially filled with the nutrient medium such that all discs (11) of the shaft are sink and rotated into the medium. Said configuration define an overlay space (23) into the vessel (1) where shaft drive mechanisms (16) are located and therefrom said central shaft (9) and peripheral shafts (10) are extended into the medium. Here, the vessel (1) is equipped with the additional gas inlet port (14) for injecting air, oxygen, carbon di-oxide or other gases into the overlay space (23) and thereby to provide additional means for mass transfer. Here, the magnetic rotating means (13) for discs' rotation are located at the bottom of the vessel and rotational means for deflector vanes along with baffle mounting ring (8) is located at the top of the culture vessel as shown in FIG. 15 (a). The medium is discharged through the outlet (1b) from and then fed into the vessel (1) through the inlet (1a) by flowing from the gas exchanger through the pumping means. In this embodiment, the bottom magnetic rotation means (13) for discs' rotation also include impelling frames to prevent settling of cells and other debris at the bottom surface of the culture vessel (1).

In another embodiment of present invention shown in FIGS. 16a, 16b and 16c, said shaft drive mechanism (16) and the magnetic rotating means (13) are mounted within the overlay space (23). The deflector vanes (12) mounted on impeller vanes molded baffle mounting ring (8) is rotatabaly mounted at the bottom of the culture vessel to prevent settling of cells and other debris at the bottom surface of the culture vessel. Further, as shown in FIG. 16 (a), in said embodiment, the gear plates are utilized for rotation of the central (9) and peripheral shafts (10). Here, the gear plate mounted on the central shaft (9) can be referred as a central gear plate (17) and the gear plates mounted on the peripheral shafts (10) can be considered as peripheral gear plates (18). The teeth of the central gear plate (17) are received into the space between the teeth of the peripheral gear plates (18) so that the rotation of the central gear plate (17) cause to rotate the peripheral gear plates (18) (refer FIG. 4(c)). During operation, the central gear plate is rotated by said magnetic rotating means (13) thereby the peripheral gear plates and hence their corresponding peripheral shafts (10) are rotated. The speed of rotation of the central shaft (9) and the peripheral shafts (10) may be varied by changing the diameter of the teeth of the central gear plate and peripheral gear plates. It is within the scope of present invention to adapt said drive shaft mechanism in preceding embodiments. In this embodiment, the bottom impeller vanes molded baffle mounting ring (8) include impelling vanes or frames to prevent settling of cells and other debris at the bottom surface of the culture vessel (1).

It is to be noted that the present invention described with reference to aforesaid embodiments is particularly for efficient cell culturing of various biological cell. However, the bioreactor system according to present invention can also used in different kind of fields as described below.

It is within the scope of present invention to configure the bioreactor system according to present invention for enzymatic treatment of variety of substrates. Enzymes have been used throughout human history and today the enzyme applications have considerable role in the heart of biotechnology processes. A large number of these biotechnology processes require a successful enzyme immobilization in terms of resistance to leaking, retention of enzyme activity as long-term storage and operational stability under adverse environmental conditions, accessibility to substrates, fast catalysis, and, in general, high enzyme immobilization density and adequate orientation. Among the different methods of immobilization, enzyme encapsulation inside of a host semi-permeable membrane or entrapment in a network matrix such as hydrogels and other polymeric materials in form of particles, capsules, fibers, etc, is of particular interest. Using the above mentioned enzyme encapsulation techniques to create or manufacture discs make the said bioreactor system capable for efficient enzymatic treatment of variety of substrates. Due to homogenized condition within support matrix, the substrates can be converted into product or other intermediate by constructing said discs (11) such that the enzymes, catalytic proteins or active sites of these proteins are coated, embedded or encapsulated on the surfaces of the discs. In this process, the bioreactor system and its component works in the same manner as described in aforesaid embodiments.

It is within the scope of present invention to configure the bioreactor system according to present invention for achieving variety of chemical or biochemical conversions or reactions by constructing said discs (11) such that variety of chemical, organic or inorganic compounds or their functional groups or active sites are coated, embedded of encapsulated on the surface of the discs (11).

Further, for configuring the bioreactor system according to present invention for treatment of effluent streams and for variety of bioremediation processes, large sized discs are constructed from suitable material to support growth of microorganisms on the surfaces to enable the use of vessel (1) similar to rotating biological contactors. The support matrix (2) can be substantially or partially covered by vessel and reactor can be operated in open environmental conditions. Duration and efficiency of the process can be improved when overgrowth of microbes on the disc surfaces is striped off or removed when the discs (11) are rotated intermingled and peripheral discs are rotated covering substantially partially the interspatial area between the discs loaded on the central shaft as discussed above.

Moreover, the bioreactor system according to present invention is also configured to utilize as bio-filter or chemical-filter that can be used to treat or clean variety of gaseous mixtures according to process requirement. For that, disc are coated with chemical, biochemical substances or living organism and the fluid flowing from the inlet port of the vessel (1) is in the gaseous form containing industrial waste gases or other volatile substances essential to be removed from the inlet gas mixtures.

The present invention is experimented and illustrated more in details in the following example. The example describes and demonstrates embodiments within the scope of the present invention. This example is given solely for the purpose of illustration and is not to be construed as limitations of the present invention, as many variations thereof are possible without departing from spirit and scope.

Example 1

The experiment for measuring mixing times for homogenous agitation of the biological material was performed in the vessel filled with 1 L culture medium into which aggregates of cells were introduced. For that, the height/diameter ratio of said culture vessel was kept 1.80, diameter of each disc was preferably kept 38 mm, peri-centric diameter of the peripheral shaft was preferably 50 mm, peri-centric diameter of the curved vanes was 85 mm and the angle of curved vanes was preferably kept at 40°. According to the rates of rotation of the vanes and discs of shafts, following readings were taken in the form of mixing times representing adequate mixing of components in the vessel. Dye decolorization technique is the simplest method and is used mainly for measurement of mixing time. It is done by adding acid (or base) in the bulk solution with one or more pH indicators. The decolorization can be examined by visual observation. The evaluation of mixing time is often subjective owing to visual observation by naked eyes or video images. The mixing time is defined as the interval time between the addition of dispersed phase and the disappearance of the last color trace.

| Volumetric capacity of the bioreactors | RPM of Baffling curved vanes | RPM of Discs | Recirculation Flow of liquid from Media-IN conduit (L/min) | Mixing time (in seconds) |
| --- | --- | --- | --- | --- |
| 1 L | 10 | 2 | 0.4 | 48 |
|  | 10 | 10 | 1 | 35 |
|  | 35 | 2 | 0.4 | 32 |
|  | 35 | 10 | 1 | 21 |

Example 2

In another experiment, said vessel was filled with 10 L culture medium. For that, the height/diameter ration of said culture vessel was kept 1.85, diameter of each disc was preferably kept 70 mm, peri-centric diameter of the peripheral shaft was preferably 96 mm, peri-centric diameter of the curved vanes was 178 mm and the angle of curved vanes was preferably kept at 40°. The procedure for measuring mixing times for adequate mixing was carried out in the same manner as described in above example by changing the rate of rotation of the vanes and discs and recirculation flow of medium. The following results were obtained.

| Volumetric capacity of the bioreactors | RPM of Baffling curved vanes | RPM of Discs | Recirculation Flow of liquid from Media-IN conduit (L/min) | Mixing time (in seconds) |
| --- | --- | --- | --- | --- |
| 10 L | 10 | 2 | 0.5 | 209 |
|  | 10 | 10 | 2 | 178 |
|  | 35 | 2 | 0.5 | 93 |
|  | 35 | 10 | 2 | 65 |

Example 3

The culturing of cells was carried out in the vessel filled with 100 L culture medium and the following results were recorded. For that, the height/diameter ration of said culture vessel was kept 2.00, diameter of each disc was preferably kept 160 mm, peri-centric diameter of the peripheral shaft was preferably 195 mm, peri-centric diameter of the curved vanes was 380 mm and the angle of curved vanes was preferably kept at 40°.

| Volumetric capacity of the bioreactors | RPM of Baffling curved vanes | RPM of Discs | Recirculation Flow of liquid from Media-IN conduit (L/min) | Mixing time (in seconds) |
|---|---|---|---|---|
| 100 L | 10 | 5 | 2 | 647 |
|  | 10 | 15 | 8 | 501 |
|  | 35 | 5 | 2 | 267 |
|  | 35 | 15 | 8 | 188 |

Observation:

From aforesaid results, it was noted that by increasing the RPM of vanes and disc and recirculation flow of medium in conduit, the mixing times was substantially reduced. Thus, using optimum rotational speeds with present apparatus greatly simplifies the procedure for culturing cells on continuous and large scale. It is within the scope of present invention to improve mixing by changing in other parameters like dimension of the vessel, angle of the vanes etc.

All of the disclosed and claimed apparatus and methods can be made and executed without undue experimentation in light of the present disclosure. While the system, apparatus and methods of this invention have been described in terms of preferred embodiments, it will be apparent to those of skill in the art that variations can be applied to the methods, system and apparatus and in the steps or in the sequence of steps of the methods described herein without departing from the concept, spirit and scope of the invention.

LIST OF REFERENCE NUMERALS

Culture Vessel (1)
Inlet Port (1a)
Outlet Port (1b)
Support Matrix (2)
Pumping Means (3)
Gas Exchange Means (4)
Main Conduit (5)
Recirculation loop (A)
Support Framework (6)
Hollow Centre (6a, 7a)
Spokes (6b, 6d, 7b)
Inner Circular Plate (6c)
Baffle Supporting Frame (6e)
Peripheral Shaft Mounting Frame (7)
Baffle Mounting Plate (8)
Central Shaft (9)
Peripheral Shaft (10)
Disc (11)
Interspatial Space (11a)
Deflector Vanes (12)
Magnetic Rotation Means (13)
Conduits (14)
Sensor (15)
Shaft Drive Mechanism (16)
Central Gear Plate (17)
Peripheral Gear Plate (18)
Kinetic Energy Means (19)
Commercial cell carriers (20)
Fluid Permeable Molded Disc Frame (21)
Impeller vanes (22)
Overlay Space (23)

I claim:

1. A bioreactor system for processing, propagating, culturing, entrapping or encapsulating a biological material, cells, chemicals or enzymes and comprising:

at least one culture vessel (1) wherein a process for culturing cells takes place, the culture vessel (1) arranged to contain fluid medium having an inlet port (1a) and an outlet port (1b) and contain at least one fluid IN/Out conduits (14) for the purpose of supplying fluid therein and discharging fluid therefrom after completion of culturing process to maintain desired metabolic state of the culture process including inoculation conduit and sampling conduit and contains at least one sensing element (15) for temperature, pressure, pH, oxygen, carbon dioxide and other metabolites important to be measured and controlled during process;

at least one support matrix (2) contained within the culture vessel (1) wherein said support matrix (2) comprises of at least one rotatable central shaft (9) being centrally and longitudinally extended in to the vessel (1), at least one support framework ring (6) to rotatable locate the central shaft (9), at least one shaft mounting frame (6c), one or more rotatable peripheral shafts (10) radially and parallelly extended into the culture vessel (1) with respect to the central shaft (9), a plurality of stacked spaced apart discs (11) centrally and longitudinally loaded on the central shaft (9) and the peripheral shafts (10) for providing substratum for cell attachment and cell growth, a spacer located between two succeeding discs (11) for defining interspatial space (11a), one or more baffling means to create radial fluid flow to improve the mixing condition within the vessel (1), and one or more rotating means (13) for rotation of central shaft (9), peripheral shafts (10) and baffling means and a shaft driving mechanism (16) to support smooth rotation of central shaft (9) and peripheral shafts (10);

at least one recirculation loop conduit (5) externally and fluidly connecting between said inlet port (1a) and the outlet port (1b) to support aseptic transfer of fluids to and from the culture vessel (1) for creating recirculation loop (A);

at least one fluid pumping means (3) to create desired fluid flow through the recirculation loop (A) for desired operation of the process installed at the recirculation loop conduit (5) and the pumping means to transfer the fluids including media, feeds, buffers and other process needs;

at least one gas exchange means (4) installed at recirculation loop conduit (5) for efficient mass transfer of fluids from one phase to another phase during circulation of fluid through recirculation loop (A);

wherein each disc (11) loaded on the peripheral shafts (9) in one geometric plane is configured to partially and rotatably invade and occupy the interspatial space (11a) created between two successive discs (11) loaded on the central shaft (9); and the baffling means consist of one or more rotatable deflector vanes (12) extended along the axial length of the culture vessel (1) to radially and parallelly surround the discs (11) loaded on the central (9) and peripheral shafts (10) and mounted on baffle mounting ring (8).

2. The bioreactor system as claimed in claim 1, wherein the system comprises at least one fluid reservoir to provide source of fluid according to process needs.

3. The bioreactor system as claimed in claim 1, wherein the system comprises at least one process control system to monitor and control the process parameters during culturing process.

4. The bioreactor system as claimed in claim 1, wherein the system comprises one or more kinetic energy source (19) for the rotation of shafts and baffling means through the rotating means (13).

5. The bioreactor system as claimed in claim 1, wherein the culture vessel (1) is equipped with one or more weight sensing element for accurate measurement of fluid content and fluid volume in bioreactor culture vessel (1).

6. The bioreactor system as claimed in claim 1, wherein the culture vessel (1) is equipped with at least one gas supply conduit and gas exhaust conduit or air vent.

7. The bioreactor system as claimed in claim 1, wherein the discs (11) are constructed from fibrous or porous material.

8. The bioreactor system as claimed in claim 1, wherein the discs (11) are constructed with apertures or holes to provide additional turbulence and more efficient fluid flow.

9. The bioreactor system as claimed in claim 1, wherein the disc (11) loaded on the central shaft (9) are directly surrounded by one or more deflector vanes (12) as baffling vanes when no peripheral shafts are located surrounding the central shaft (9).

10. The bioreactor system as claimed in claim 1, wherein six peripheral shafts (10) are located surrounding central shaft (9) thereby at a time in one geometric plane the discs (11) loaded on three alternative peripheral shafts partially and substantially invade and occupies the interspatial space (11a) created between two successive discs (11) loaded on the central shaft (9).

11. The bioreactor system as claimed in claim 1, wherein one or two peripheral shafts (10) are located surrounding central shaft (9) thereby at a time in one geometric plane discs (11) loaded on one peripheral shafts (10) partially and substantially occupy the interspatial space (11a) created between two successive discs loaded on the central shaft (9).

12. The bioreactor system as claimed in claim 1, wherein three peripheral shafts (10) are located surrounding the central shaft (9) thereby discs (11) loaded on the peripheral shafts (10) partially and substantially occupies the interspatial space (11a) created between two successive discs loaded on the central shaft (9).

13. The bioreactor system as claimed in claim 1, wherein more than six peripheral shafts (10) are located surrounding central shaft (9) in different successive pericentric diameters thereby discs loaded on three alternative peripheral shafts partially and substantially occupies the interspatial space created between two successive discs loaded on the central shaft (9) and the discs of outermost peripheral shafts (10) partially invade in interspatial space (11a) between successive discs of inner circle peripheral shafts.

14. The bioreactor system of claim 1, wherein the shape of the deflector vanes (12) is substantially flat, for maximum tangential fluid flow.

15. The bioreactor system as claimed in claim 1, wherein the shape of the deflector vanes is curved, twisted and/or angled, to provide additional radial and axial flow.

16. The bioreactor system as claimed in claim 1, wherein the deflector vanes (12) are molded on impeller vanes molded baffle mounting plate (8).

17. The bioreactor system as claimed in claim 1, wherein the baffling means are fixedly loaded on the central shaft (9) and takes rotational energy from the rotation of the central shaft (9).

18. The bioreactor system as claimed in claim 1 wherein the baffling means are rotatably loaded on the central shaft (9) and gain the rotational energy from the rotational means mounted on the baffling means, thereby the rotational speed of the deflector vanes (12) loaded on the baffle support ring (8) is selectively and controlled independently from the rotation of shafts.

19. The bioreactor system as claimed in claim 1, wherein the baffling means are loaded at upstream end of the vessel (1) so as the deflector vanes (12) are raised radially from upstream end to downstream end and surrounding the support matrix (2).

20. The bioreactor system as claimed in claim 1, wherein the baffling means are loaded at downstream end of the vessel (1) so as the deflector vanes (12) are raised radially from downstream end to upstream end and surrounding the support matrix (2).

21. The bioreactor system as claimed in claim 1, wherein the deflector vanes (12) on baffling means are spiral in shape and loaded fixedly on the central shaft (9) so that rotational energy for baffling means is gained from flow of fluid flowing from one end to other end of the vessel (1) and the rotation of baffling means causes the central and peripheral shafts to rotate without external rotation means.

22. The bioreactor system as claimed in claim 1, wherein wall of the culture vessel (1) is constructed to accommodate the gas exchange means for direct and quick mass transfer between fluids including oxygen and carbon dioxide gases.

23. The bioreactor system as claimed in claim 22, wherein said gas exchange means includes a gas permeable silicon tubing and/or gas permeable membranes.

24. The bioreactor system as claimed in claim 1, wherein the wall of the culture vessel (1) is constructed to accommodate temperature regulating element.

25. The bioreactor system as claimed in claim 24, wherein said temperature regulating element includes a water circulation jacket and a silicon rubber heater.

26. The bioreactor system as claimed in claim 1, wherein the culture vessel (1) is constructed from non-disposable material and accommodates disposable support matrix.

27. The bioreactor system as claimed in claim 1, wherein the culture vessel (1) is constructed from non-disposable material and accommodates non-disposable support matrix components.

28. The bioreactor system as claimed in claim 1, wherein one or more bioreactor system components are constructed from suitable polymeric material so that the bioreactor can be used as a single use disposable system.

29. The bioreactor system as claimed in claim 1, wherein one or more bioreactor system components are constructed from gamma radiation stable suitable polymeric material so that the bioreactor is used pre-sterilized and as a single use disposable system.

30. The bioreactor system as claimed in claim 1, wherein one or more bioreactor system components are constructed from steam sterilization stable suitable polymeric material so that the bioreactor is used after steam sterilization and as a single use disposable system.

31. The bioreactor system as claimed in claim 1, wherein the culture vessel (1) is positioned substantially horizontal while in use and during operation.

32. The bioreactor system as claimed in claim 1, wherein the culture vessel (1) is positioned substantially vertical while in use and during operation.

33. The bioreactor system as claimed in claim 1, wherein the culture vessel (1) is completely filled by fluid while in use and during operation.

34. The bioreactor system as claimed in claim 1, wherein the culture vessel (1) is partially filled by fluid to create overlay space (23) for additional gas exchange while in use and during operation.

35. The bioreactor system as claimed in claim 1, wherein two or more culture vessels (1) are arranged in parallel or in series along the fluid path.

36. The bioreactor system as claimed in claim 1, wherein a vibrating tool or sonication probe are inserted into the support matrix (2) through the culture vessel wall to effectively apply vibrating motion to the surfaces of the support matrix (2) thereby to detach the biological cells adhered on the discs' surfaces or active ingredient or particles coated on the surface of the support matrix discs (11).

37. The bioreactor system as claimed in claim 1, wherein the support matrix (2) is partially covered or contained within the culture vessel.

38. A method for operating bioreactor system of claim 1 for cultivating biological cells comprising:
A. adding an amount of culture medium to the culture vessel (1);
B. adding materials to the culture medium to promote the growth of the biological cells;
C. starting a gas supply by the gas exchange means (4);
D. adding biological cells to the vessel (1) to seed the culture process;
E. starting the cultivation process by applying a kinetic energy source to the rotational means (13) loaded in the support matrix (2) for shaft rotation and for the rotation of baffling means;
F. measuring and controlling culture parameters at optimum level using sensing elements (15), process control means, pumping means and conduits provided for addition of process fluids at controlled rate;
G. partially collecting a product stream fluid at a controlled rate from the vessel (1) through the fluid outlet conduit and adding fresh nutrient rich medium or fluids at controlled rate to maintain constant fluid volume and to achieve steady state operation of process in perfusion mode of bioprocessing;
H. starting harvesting of the bioreactor vessel (1) when a desired amount of product is produced.

39. The method as claimed in claim 38, wherein the biological material, enzymes, catalytic proteins or active sites of proteins are coated, embedded or encapsulated on the surfaces of the said discs (11) and performing the steps A to H.

40. The method as claimed in claim 38, wherein chemical, organic or inorganic compounds or their functional groups or active sites are coated, embedded or encapsulated on the surfaces of the said discs (11) and performing the steps A to H.

41. The method as claimed in claim 38, wherein constructing large sized discs (11) from suitable material to support growth of microorganisms on the surfaces to enable the use of bioreactor system for the treatment of effluent streams and for variety of bioremediation processes and performing the steps A to H.

42. The method as claimed in claim 38, wherein coating said discs (11) with chemical, biochemical substances or living organism and flowing the fluid in the gaseous form from the inlet port of the vessel containing industrial waste gases or other volatile substances essential to be removed from the inlet gases for working of said reactor as bio-filter or chemical-filter and treating or cleaning variety of gaseous mixtures according to the process requirement and performing the steps A to H.

* * * * *